United States Patent
Shelton, IV et al.

(10) Patent No.: US 10,485,618 B2
(45) Date of Patent: Nov. 26, 2019

(54) METHODS, SYSTEMS, AND DEVICES FOR LIMITING TORQUE IN ROBOTIC SURGICAL TOOLS

(71) Applicant: Ethicon LLC, Guaynabo, PR (US)

(72) Inventors: Frederick E. Shelton, IV, Hillsboro, OH (US); Jason L. Harris, Lebanon, OH (US); Jeffrey S. Swayze, Hamilton, OH (US); Michael J. Vendely, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

(21) Appl. No.: 15/950,276

(22) Filed: Apr. 11, 2018

(65) Prior Publication Data

US 2018/0228561 A1 Aug. 16, 2018

Related U.S. Application Data

(63) Continuation of application No. 15/237,661, filed on Aug. 16, 2016, now Pat. No. 10,045,827.

(51) Int. Cl.
| | |
|---|---|
| *B25J 9/18* | (2006.01) |
| *A61B 34/30* | (2016.01) |
| *A61B 90/00* | (2016.01) |
| *F16H 3/22* | (2006.01) |
| *A61B 34/35* | (2016.01) |
| *F16H 63/00* | (2006.01) |
| *F16H 3/20* | (2006.01) |

(52) U.S. Cl.
CPC ............. *A61B 34/30* (2016.02); *A61B 34/35* (2016.02); *A61B 90/03* (2016.02); *F16H 3/22* (2013.01); *A61B 2090/031* (2016.02); *F16H 3/20* (2013.01); *F16H 63/00* (2013.01)

(58) Field of Classification Search
CPC .... A61B 34/30; A61B 2090/031; A61B 34/70
See application file for complete search history.

(56) References Cited

U.S. PATENT DOCUMENTS

| | | | | |
|---|---|---|---|---|
| 6,017,354 | A | * | 1/2000 | Culp .................. A61B 17/1626 604/22 |
| 7,653,970 | B1 | | 2/2010 | Lai |

(Continued)

FOREIGN PATENT DOCUMENTS

WO WO 2015020906 A1 2/2015

OTHER PUBLICATIONS

Correlated Solutions, "Principle of Digital Image Correlation," 2013 (http://correlatedsolutions.com/digital-image-correlation/).

(Continued)

*Primary Examiner* — Karen Masih
(74) *Attorney, Agent, or Firm* — Mintz Levin Cohn Ferris Glovsky and Popeo, P.C.

(57) ABSTRACT

Various exemplary methods, systems, and devices for limiting torque in robotic surgical tools are provided. In general, a surgical tool can be configured to releasably and removably couple to a robotic surgical system. The robotic surgical system can include a motor configured to provide torque to the surgical tool to drive two different functions of the surgical tool. The surgical tool can include two torque limiting mechanisms, each associated with the motor, each associated with one of the functions, and each configured to limit an amount of the torque from the motor that drives the function associated therewith.

19 Claims, 13 Drawing Sheets

(56) References Cited

U.S. PATENT DOCUMENTS

| | | | |
|---|---|---|---|
| 8,114,345 B2 | 2/2012 | Dlugos, Jr. et al. | |
| 8,882,792 B2 | 11/2014 | Dietz et al. | |
| 8,915,842 B2 | 12/2014 | Weisenburgh, II et al. | |
| 8,931,682 B2 | 1/2015 | Timm et al. | |
| 8,945,098 B2 | 2/2015 | Seibold et al. | |
| 2008/0081948 A1 | 4/2008 | Weisenburgh et al. | |
| 2011/0112568 A1* | 5/2011 | Frecker | A61B 17/29 606/205 |
| 2011/0118709 A1 | 5/2011 | Burbank | |
| 2011/0118778 A1 | 5/2011 | Burbank | |
| 2011/0284254 A1* | 11/2011 | Moore | B23Q 17/007 173/2 |
| 2012/0150192 A1 | 6/2012 | Dachs | |
| 2013/0282052 A1 | 10/2013 | Aranyi et al. | |
| 2013/0331646 A1* | 12/2013 | Pell | A61B 17/29 600/106 |
| 2014/0005662 A1 | 1/2014 | Shelton | |
| 2014/0005718 A1 | 1/2014 | Shelton, IV et al. | |
| 2018/0049816 A1 | 2/2018 | Shelton | |

OTHER PUBLICATIONS

U.S. Appl. No. 15/131,963 entitled "Method for Operating a Surgical Instrument" filed Apr. 18, 2016.

U.S. Appl. No. 15/177,430 entitled "Surgical Instrument With User Adaptable Techniques" filed Jun. 9, 2016.

International Search Report for Intl. App. PCT/US2017/046457 dated Nov. 13, 2017 (5 pages).

\* cited by examiner

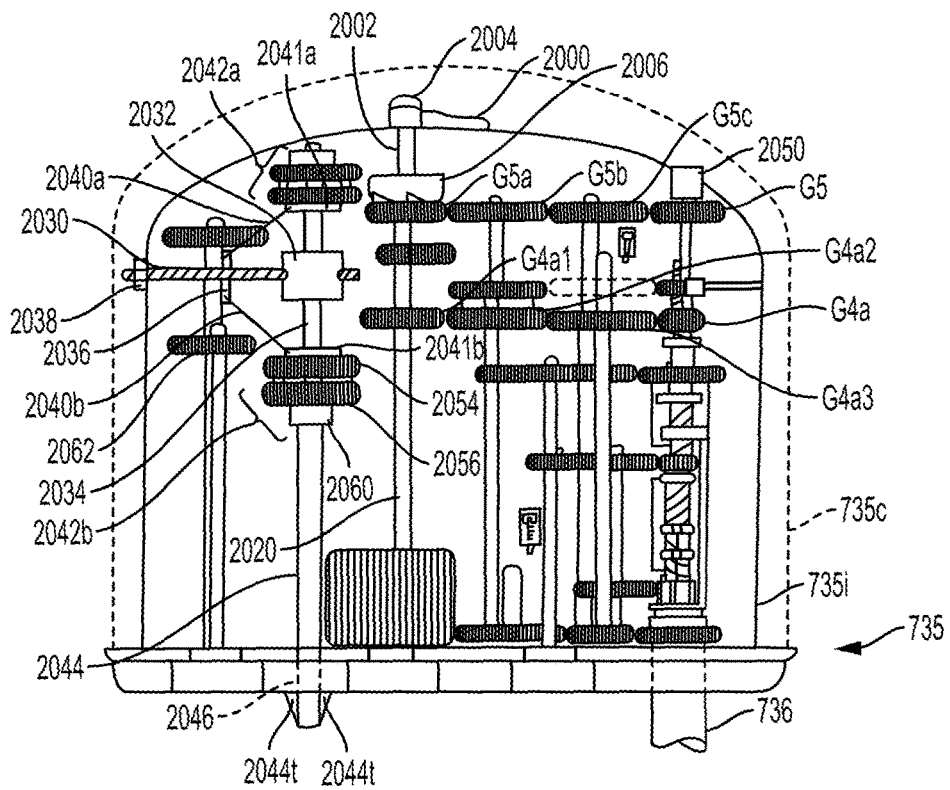
FIG. 10
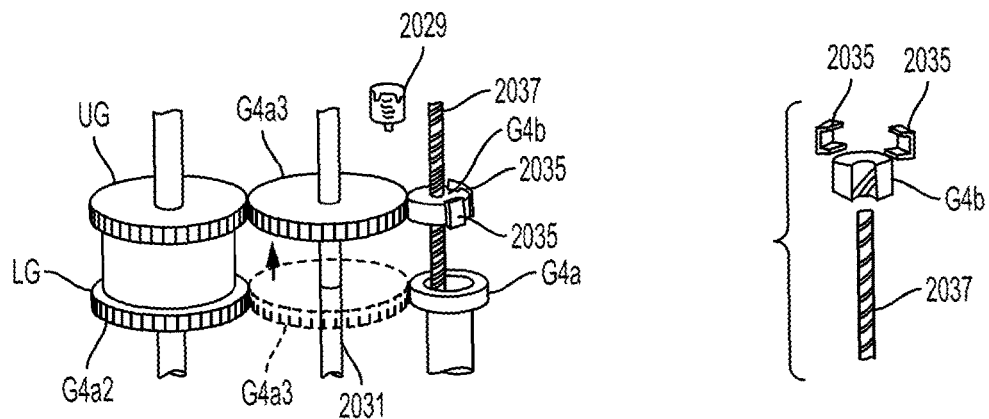
FIG. 11
FIG. 12

METHODS, SYSTEMS, AND DEVICES FOR LIMITING TORQUE IN ROBOTIC SURGICAL TOOLS

CROSS REFERENCE TO RELATED APPLICATIONS

The present application claims priority to U.S. patent application Ser. No. 15/237,661 entitled "Methods, Systems, and Devices for Limiting Torque in Robotic Surgical Tools" filed Aug. 16, 2016, which is hereby incorporated by reference in its entirety.

FIELD

Methods and devices are provided for robotic surgery, and in particular for methods, systems, and devices for limiting torque in robotic surgical tools.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

In general, methods, systems, and devices for limiting torque in robotic surgical tools are provided.

In one aspect, a surgical system is provided that in one embodiment a tool driver of a robotic surgical system. The tool driver is configured to releasably and replaceably couple to a surgical tool including an elongate shaft with an end effector at a distal end thereof. The tool driver includes a first motor, a first actuator configured to be driven by the first motor to actuate a first function of the end effector, a first torque limiting mechanism that sets a first torque threshold for the first actuator, a second actuator configured to be driven by the first motor to actuate a second function of the end effector, and a second torque limiting mechanism that sets a second torque threshold for the first actuator that is different from the first torque threshold.

The surgical system can have any number of variations. For example, the first motor can be configured to selectively shift between engagement with the first actuator to drive the first actuator without driving the second actuator and engagement with the second actuator to drive the second actuator without driving the first actuator.

For another example, the first function can be closing of the end effector at a first speed, and the second function can be closing the end effector at a second speed that is greater than the first speed. In at least some embodiments, the first torque threshold can be greater than the second torque threshold.

For yet another example, the tool driver can include a third torque limiting mechanism that sets a third torque threshold for the first actuator that is different from the first torque threshold. The first torque limiting mechanism but not the third torque limiting mechanism can be configured to be engaged by the first actuator when the first actuator is being driven to rotate in a first direction, and the third torque limiting mechanism but not the first torque limiting mechanism can be configured to be engaged by the first actuator when the first actuator is being driven in to rotate in a second direction that is opposite to the first direction. In at least some embodiments, the tool driver can include a fourth torque limiting mechanism that sets a fifth torque threshold for the second actuator that is different from the second torque threshold. The second torque limiting mechanism but not the fourth torque limiting mechanism can be configured to be engaged by the second actuator when the second actuator is being driven to rotate in the first direction, and the fourth torque limiting mechanism but not the second torque limiting mechanism can be configured to be engaged by the second actuator when the second actuator is being driven in to rotate in the second direction that is opposite to the first direction.

For another example, the first actuator can have a first mating element, the first torque limiting mechanism can have a second mating element, engagement of the first mating element with the second mating element during the driving of the first actuator by the motor can define the first torque threshold, the second actuator can have a third mating element, the second torque limiting mechanism can have a fourth mating element, and engagement of the third mating element with the fourth mating element during the driving of the second actuator by the motor can define the second torque threshold.

For still another example, the tool driver can include a first shaft having the first and second actuators and the first and second limiting mechanisms attached thereto along a longitudinal length thereof. In at least some embodiments, the first motor can be configured to rotate a second shaft having first and second drive disks attached thereto along a longitudinal length thereof, the first drive disk can be operatively coupled to the first actuator such that rotation of the second shaft causes the first actuator to rotate, and the second drive disk can be operatively coupled to the second actuator such that rotation of the second shaft causes the second actuator to rotate. Additionally or alternatively, in at least some embodiments, the tool driver can include a third actuator attached to the shaft along a longitudinal length thereof, a second motor configured to drive the third actuator to actuate a third function of the actuator, and a third torque limiting mechanism that sets a third torque threshold for the third actuator. In at least some embodiments, the first function can be closing of the end effector at a first speed, the second function can be closing the end effector at a second speed that is greater than the first speed, and the third function can be firing of the end effector.

For yet another example, the first motor can include a single motor, and the tool driver can include one or more additional motors that are each configured to drive one or more additional actuators of the tool driver that each actuate a function of the end effector that is different from the first and second functions.

For another example, the first and second actuators can each include a rotatable gear.

In another embodiment, a surgical system is provided that includes a surgical tool including an elongate shaft having an end effector at a distal end thereof, and a tool driver of a robotic surgical system. The tool driver is configured to releasably couple to the surgical tool. The tool driver includes a first actuator configured to be actuated to cause the end effector to perform a first function, a second actuator configured to be actuated to cause the end effector to perform a second function, a first motor configured to selectively actuate each of first and second actuators, a first torque limiting mechanism configured to limit an amount of torque applied by the motor to the first actuator, and a second torque limiting mechanism configured to limit an amount of torque applied by the motor to the second actuator.

The surgical system can vary in any number of ways. For example, the first motor can be configured to selectively shift between engagement with the first actuator to drive the first actuator without driving the second actuator and engagement with the second actuator to drive the second actuator without driving the first actuator. For another example, the first function can be closing of the end effector at a first speed, and the second function can be closing the end effector at a second speed that is greater than the first speed. For yet another example, the first motor can include a single motor, and the tool driver can include one or more additional motors that are each configured to drive one or more additional actuators of the tool driver that are each configured to be actuated to cause the end effector to perform a function of that is different from the first and second functions.

In another aspect, a surgical method is provided that in one embodiment includes advancing an end effector of a surgical tool into a body of a patient using a robotic surgical system. The surgical tool is releasably and replaceably coupled to the robotic surgical system. The surgical method also includes actuating a single motor of the robotic surgical system to drive a first actuator of the robotic surgical system and thereby cause the end effector to execute a first function in the body of the patient. The motor has a maximum torque output, and an amount of torque applied by the motor to the first actuator is prevented from exceeding a first torque threshold that is less than the maximum torque output. The surgical method also includes actuating the single motor of the robotic surgical system to cause the end effector to execute a second function in the body of the patient that is different from the first function. An amount of torque applied by the motor to the second actuator is prevented from exceeding a second torque threshold that is less than the maximum torque output and that is different from the first torque threshold.

The surgical method can vary in any number of ways. For example, the amount of torque applied by the motor to the first actuator can be prevented from exceeding the first torque threshold when the motor drives rotation of the first actuator in a first direction, and the amount of torque applied by the motor to the first actuator when the motor drives rotation of the first actuator in a second direction can be prevented from exceeding a third torque threshold that is different from the first torque threshold. The first direction can be opposite to the second direction. The amount of torque applied by the motor to the second actuator can be prevented from exceeding the second torque threshold when the motor drives rotation of the second actuator in the first direction, and the amount of torque applied by the motor to the second actuator when the motor drives rotation of the second actuator in the second direction can be prevented from exceeding a fourth torque threshold that is different from the second torque threshold.

For another example, the first function can be closing of the end effector at a first speed, and the second function can be closing the end effector at a second speed that is greater than the first speed.

BRIEF DESCRIPTION OF DRAWINGS

This invention will be more fully understood from the following detailed description taken in conjunction with the accompanying drawings, in which:

FIG. 10 is a partial cross-sectional side view of the puck of FIG. 5 in a bailout state;

FIG. 11 is a perspective view of engaged gears of the puck of FIG. 5 including a shiftable gear;

FIG. 12 is an exploded partially cross-sectional view of one of the gears of FIG. 11 and a shaft on which the gear is movably attachable;

DETAILED DESCRIPTION

Figure 1:
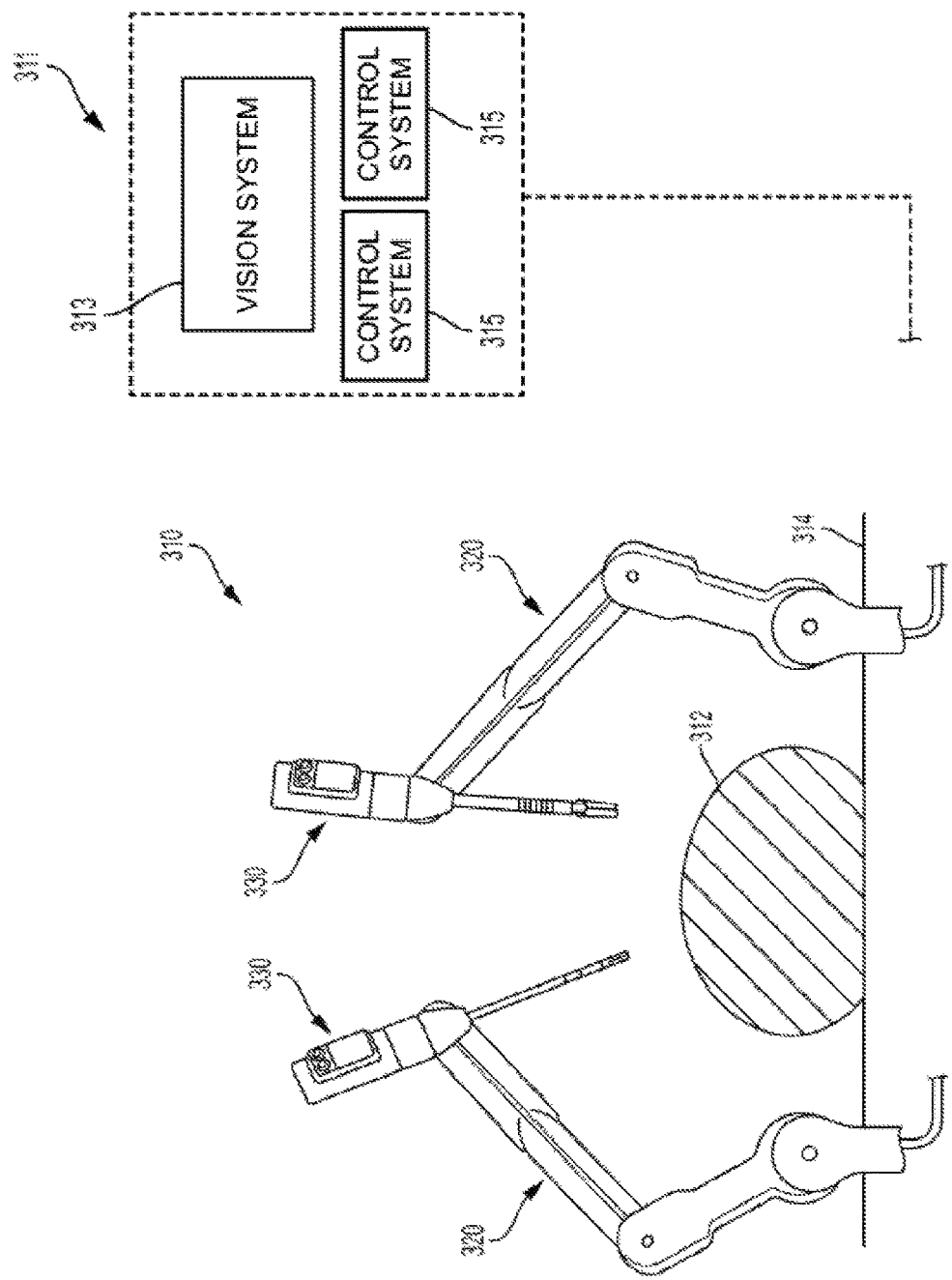
FIG. 1 is a perspective view of one embodiment of a surgical robotic system that includes a patient-side portion and a user-side portion.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods, systems, and devices for limiting torque in robotic surgical tools are provided. In general, a surgical tool can be configured to releasably and removably couple to a robotic surgical system. The robotic surgical system can include a motor configured to provide torque to the surgical tool to drive two different functions of the surgical tool. The two different functions can be functions that are not performed at the same time, e.g., the functions can be mutually exclusive. The motor can thus be configured to selectively drive one of two functions of the surgical tool, which may allow the surgical tool to perform more functions than traditional surgical tools since one motor can be configured to drive two different functions of the surgical tool instead of just one function of the surgical tool. The surgical tool can include two torque limiting mechanisms, each associated with the motor, each associated with one of the functions, and each configured to limit an amount of the torque from the motor that drives the function associated therewith. The torque limiting mechanisms may thus prevent the motor from providing too much torque to the surgical tool. If too much torque is provided to the surgical tool, the function may not be effected as desired and/or damage may be caused to the surgical tool and/or to the patient on which the surgical tool is being used. The torque limiting mechanisms may serve as a backup safety mechanism to the robotic surgical system in the event that the robotic surgical system does not appropriately limit torque output of the motor according to its control programming, which may happen for any number of reasons, such as inadvertent system malfunction or electrical control signals being processed too slowly or too quickly to effect desired torque output of the motor. The torque limiting mechanisms can be mechanical members so as to not be reliant on electrical control signals to effect torque limiting.

The robotic surgical system can include one or more motors in addition to the one motor configured to drive the two different functions. Each of the additional one or more motors can be configured to drive a function of the surgical tool that is different from each of the other functions of the surgical tool. The robotic surgical system may thus be configured to drive at least three different functions of the surgical tool, which may allow for more versatile use of the surgical tool in a body of a patient and/or allow two or more of the functions to be performed at the same time since the two or more functions can be simultaneously, respectively driven by two or more of the motors.

Functions of the surgical tool can include a function of an end effector of the surgical tool. Functions of the end effector can include, for example, a quick close of the end effector (e.g., closing jaws of the surgical tool at a first speed), a slower close of the end effector (e.g., closing jaws of the surgical tool at a second speed that is less than the first speed associated with quick close), articulation of the end effector relative to an elongate shaft of the surgical tool (e.g., angling the end effector relative to a longitudinal axis of the elongate shaft), rotation of the end effector relative to the elongate shaft (e.g., rotation of the end effector about a longitudinal axis thereof), and rotation of the end effector and the shaft as a unit about the longitudinal axis of the shaft. In an exemplary embodiment, the two different functions configured to be driven by the one motor include the quick close of the end effector and the slower close of the end effector. Quick close and slower close may thus be prevented from being driven at the same time since the one motor will be shifted to drive only one or the other. Providing torque limiting mechanisms for each of the quick close and slower close functions may allow for the same motor to drive both functions while providing a different amount of maximum torque to the surgical tool to drive each of the functions and thereby allow the two different closure functions to be performed properly.

Robotic Surgical Systems

The systems, devices, and methods disclosed herein can be implemented using a robotic surgical system.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

FIG. 1 is a perspective view of one embodiment of a surgical robotic system 300 that includes a patient-side portion 310 that is positioned adjacent to a patient 312, and a user-side portion 311 that is located a distance from the patient, either in the same room and/or in a remote location. The patient-side portion 310 generally includes one or more robotic arms 320 and one or more tool assemblies 330 that are configured to releasably couple to a robotic arm 320. The user-side portion 311 generally includes a vision system 313 for viewing the patient 312 and/or surgical site, and a control system 315 for controlling the movement of the robotic arms 320 and each tool assembly 330 during a surgical procedure.

The control system 315 can have a variety of configurations and can be located adjacent to the patient, e.g., in the operating room, remote from the patient, e.g., in a separate control room, or the control system 315 can be distributed at two or more locations. For example, a dedicated system control console can be located in the operating room, and a separate console can be located in a remote location. The control system 315 can include components that enable a user to view a surgical site of a patient 312 being operated on by the patient-side portion 310 and/or to control one or more parts of the patient-side portion 310 (e.g., to perform a surgical procedure at the surgical site 312). In some embodiments, the control system 315 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 320 and tool assemblies 330.

The patient-side portion can also have a variety of configurations. As depicted in FIG. 1, the patient-side portion 310 can couple to an operating table 314. However, in some embodiments, the patient-side portion 310 can be mounted to a wall, to the ceiling, to the floor, or to other operating room equipment. Further, while the patient-side portion 310 is shown as including two robotic arms 320, more or fewer robotic arms 320 may be included. Furthermore, the patient-side portion 310 can include separate robotic arms 320 mounted in various positions, such as relative to the surgical table 314 (as shown in FIG. 1). Alternatively, the patient-side portion 310 can include a single assembly that includes one or more robotic arms 320 extending therefrom.

Figure 2:
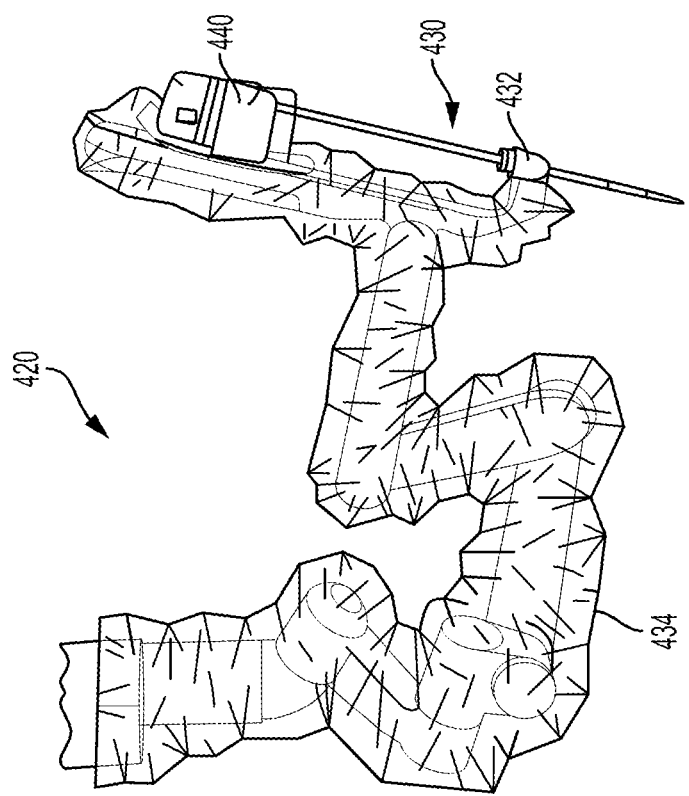
FIG. 2 is a perspective view of one embodiment of a robotic arm of a surgical robotic system with a surgical tool releasably and removably coupled to the robotic arm.

FIG. 2 illustrates one embodiment of a robotic arm 420 and a tool assembly 430 releasably coupled to the robotic arm 420. The robotic arm 420 can support and move the associated tool assembly 430 along one or more mechanical degrees of freedom (e.g., all six Cartesian degrees of freedom, five or fewer Cartesian degrees of freedom, etc.).

The robotic arm 420 can include a tool driver 440 at a distal end of the robotic arm 420, which can assist with controlling features associated with the tool assembly 430. The robotic arm 420 can also include an entry guide 432 (e.g., a cannula mount or cannula) that can be a part of or removably coupled to the robotic arm 420, as shown in FIG. 2. A shaft 436 of the tool assembly 430 can be inserted through the entry guide 430 for insertion into a patient.

In order to provide a sterile operation area while using the surgical system, a barrier 434 can be placed between the actuating portion of the surgical system (e.g., the robotic arm 420) and the surgical instruments (e.g., the tool assembly 430). A sterile component, such as an instrument sterile adapter (ISA), can also be placed at the connecting interface between the tool assembly 430 and the robotic arm 420. The placement of an ISA between the tool assembly 430 and the robotic arm 420 can ensure a sterile coupling point for the tool assembly 430 and the robotic arm 420. This permits removal of tool assemblies 430 from the robotic arm 420 to exchange with other tool assemblies 430 during the course of a surgery without compromising the sterile surgical field.

Figure 3:
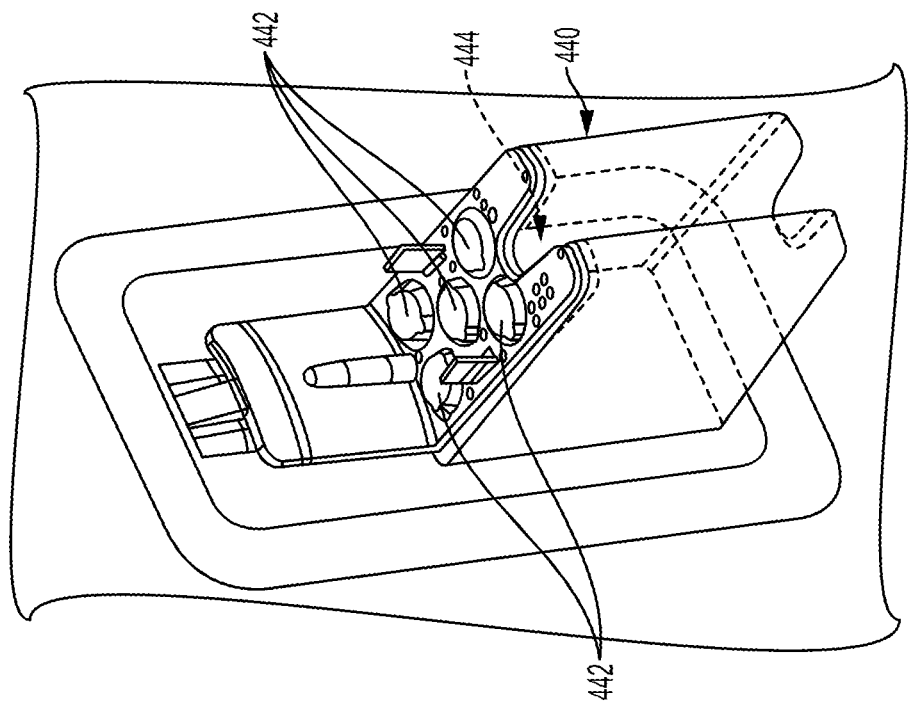
FIG. 3 is a perspective view of a tool driver of the robotic arm of FIG. 2.

FIG. 3 illustrates the tool driver 440 in more detail. As shown, the tool driver 440 includes one or more motors, e.g., five motors 442 are shown, that control a variety of movements and actions associated with the tool assembly 430, as will be described in greater detail below. For example, each motor 442 can couple to and/or interact with an activation feature (e.g., gear) associated with the tool assembly 430 for controlling one or more actions and movements that can be performed by the tool assembly 430, such as for assisting with performing a surgical operation. The motors 442 are accessible on the upper surface of the tool driver 440, and thus the tool assembly is configured to mount on top of the tool driver 440 to couple thereto. The tool driver 440 also includes a shaft-receiving channel 444 formed in a sidewall thereof for receiving the shaft of the tool assembly 430. In other embodiments, the shaft can extend through on opening in the tool driver 440, or the two components can mate in various other configurations.

Figure 4:
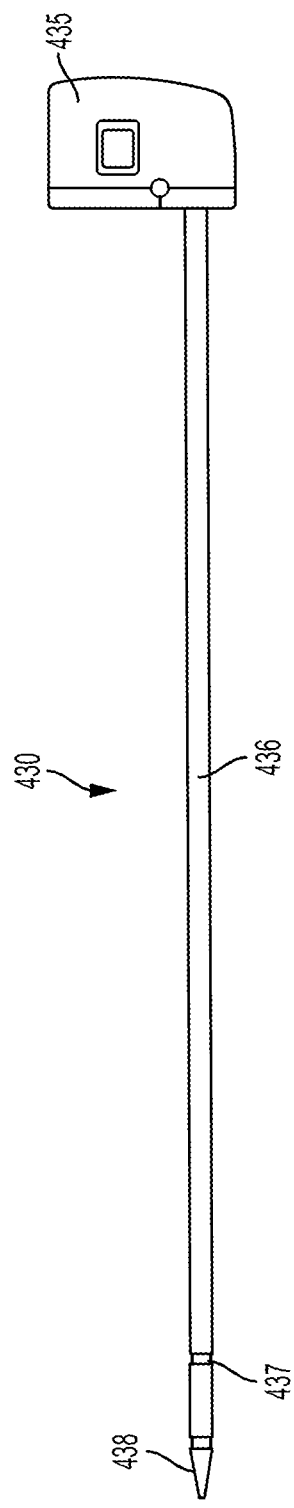
FIG. 4 is a side view of the surgical tool of FIG. 2 uncoupled from the robotic arm, the tool including a shaft extending from a puck at a proximal end and having an end effector located at a distal end of the shaft.

FIG. 4 illustrates the tool assembly 430 uncoupled from the robotic arm 420. The tool assembly 430 includes a housing or puck 435 coupled to a proximal end of the shaft 436 and an end effector 438 coupled to a distal end of the shaft 436. The puck 435 can include coupling features that assist with releasably coupling the puck 435 to the tool driver 440 of the robotic arm 420. The puck 435 can include gears and/or actuators that can be actuated by the one or more motors 442 in the driver 440, as will be described in greater detail below. The gears and/or actuators in the puck 435 can control the operation of various features associated with the end effector 438 (e.g., clamping, firing, rotation, articulation, energy delivery, etc.), as well as control the movement of the shaft 436 (e.g., rotation of the shaft).

The shaft 436 can be fixed to the puck 435, or it can be releasably coupled to the puck 435 such that the shaft 436 can be interchangeable with other shafts. This can allow a single puck 435 to be adaptable to various shafts 436 having different end effectors 438. The shaft 436 can include actuators and connectors that extend along the shaft and assist with controlling the actuation and/or movement of the end effector 438 and/or shaft 436. The shaft 436 can also include one or more joints or wrists 437 that allow a part of the shaft 436 or the end effector 438 to articulate relative to the longitudinal axis of the shaft 436. This can allow for fine movements and various angulation of the end effector 438 relative to the longitudinal axis of the shaft 436. The end effector 438 can include any of a variety of surgical tools, such as a stapler, a clip applier, forceps, a needle driver, a cautery device, a cutting tool, a pair of jaws, an imaging device (e.g., an endoscope or ultrasound probe), or a combined device that includes a combination of two or more various tools.

Figure 5:
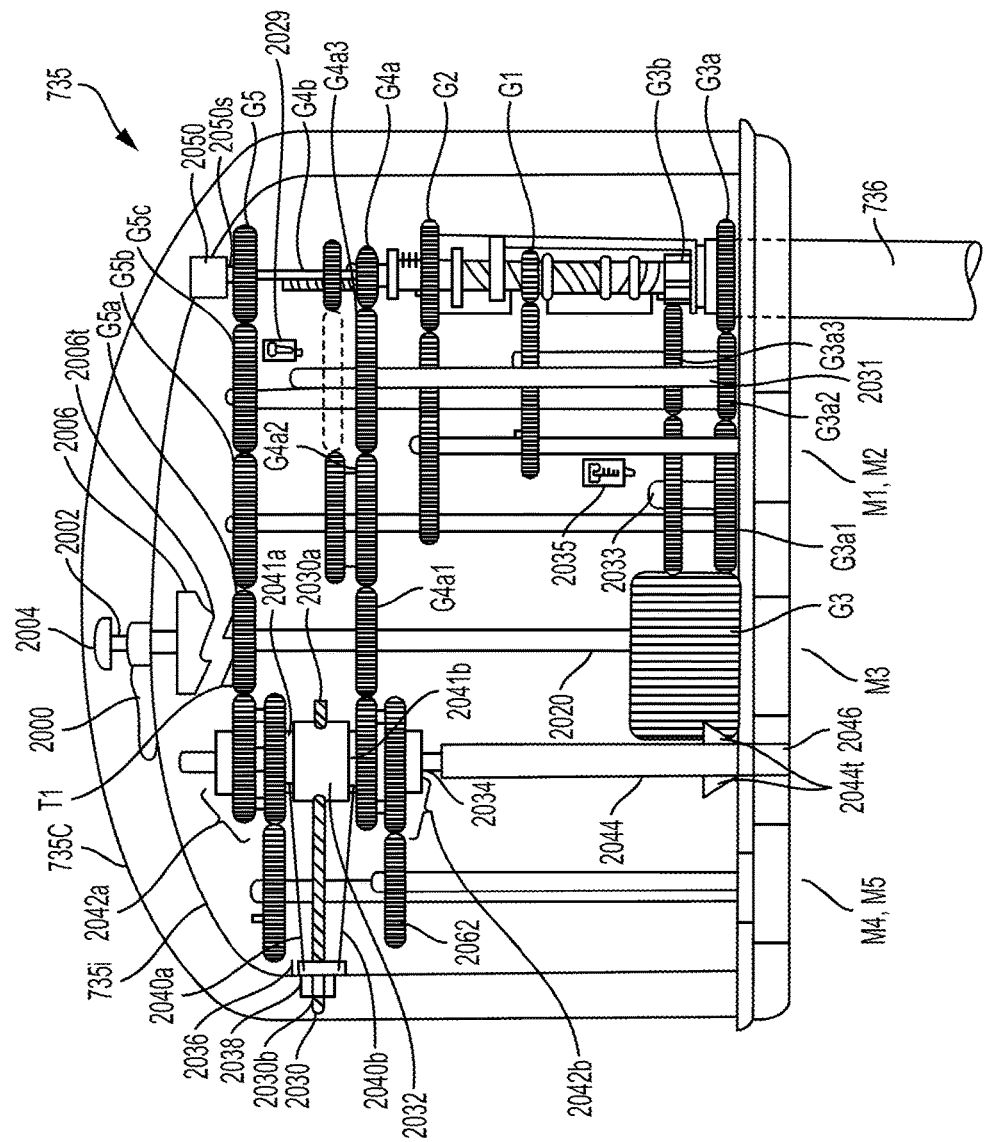
FIG. 5 is a partial cross-sectional side view of another embodiment of a puck and shaft of a surgical tool.

FIG. 5 illustrates an embodiment of a puck 735 and a proximal end of a shaft 736 extending from the puck 735. As shown in FIG. 5, the puck 735 includes a plurality of actuation gears and gear shafts that can be either directly or indirectly controlled by any one of the motors 442 associated with the driver 440. For example, as shown in FIG. 5, the puck 735 is configured to couple to five motors at the locations indicated by reference numbers M1, M2, M3, M4, and M5. In this embodiment, the puck 735 includes first and second articulation gears G1, G2 that are coupled respectively to the first and second motors M1, M2 via a series of one or more additional gears and shafts. Actuation of the first and second motors M1, M2 will rotate the articulation gears G1, G2, which in turn cause linear movement of an articulation cable in a proximal or distal direction to thereby cause articulation of an end effector at a distal end of the shaft 736 in desired left and right directions. The puck 735 also includes a shaft rotation gear G3a that is coupled to the third motor M3 via a series of one or more additional gears and shafts. Actuation of the third motor M3 will thus rotate the shaft rotation gear G3a, thereby causing rotation of the shaft 736. The third motor M3 can also be configured to shift and to couple, via a series of one or more additional gears and shafts, to a head rotation gear G3b, which will cause rotation of the end effector relative to the shaft 736. The puck 735 further includes a firm close gear G4a that is coupled to the fourth motor M4 via a series of one or more additional gears and shafts. Actuation of the fourth motor M4 will rotate the firm close gear G4a to cause linear translation of a drive screw to firmly close the jaws of the end effector. The puck 735 further includes a quick close gear G4b that can also couple to the fourth motor M4 via a series of one or more additional gears and shafts. When the fourth motor M4 is shifted into engagement with the quick close gear G4bh, actuation of the fourth motor M4 will rotate the quick close gear G4b to cause linear translation of a quick close cable to quickly close the jaws of the end effector. Finally, the illustrated puck 735 includes a firing gear G5 that is coupled to the fifth motor M5 via a series of one or more additional gears and shafts. Actuation of the fifth motor M5 will rotate the firing gear G5, thereby driving a lead screw linearly to advance a sled through the end effector, as will be discussed in more detail below.

Figure 6:
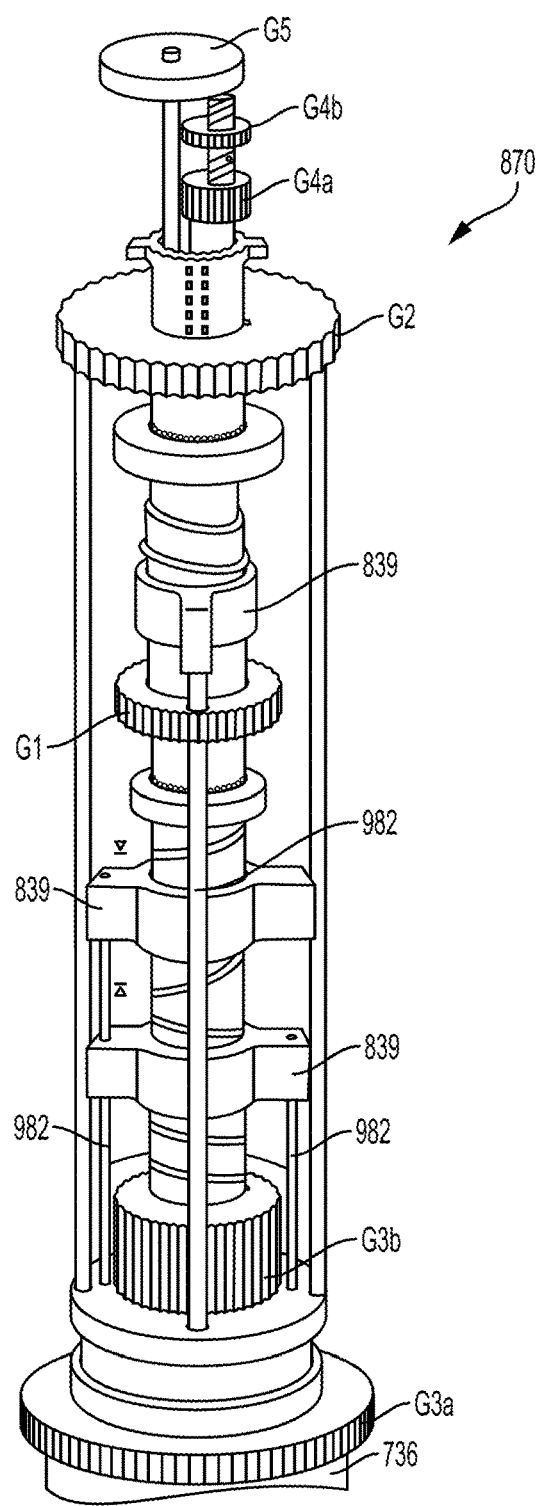
FIG. 6 is a perspective view of an actuation assembly of the puck of FIG. 5.
Figure 7:
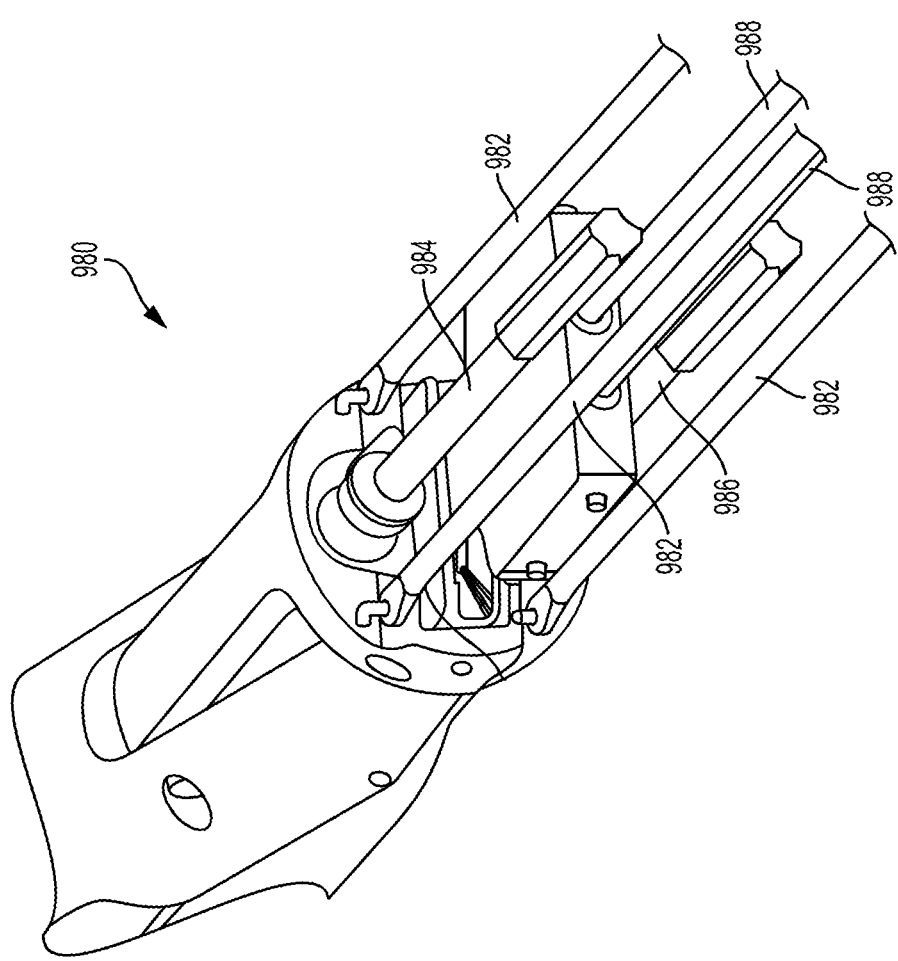
FIG. 7 is a perspective view of a wrist portion of the surgical tool of FIG. 4.

FIG. 6 illustrates actuation assembly 870 components of the puck of FIG. 5. As shown and indicated above, each of the gears G1, G2, G3, G4. G5 is coupled to an actuation shaft that extends from the actuation assembly 870 and along the shaft 736 of the tool assembly, such as for controlling the movements of the end effector. FIG. 7 illustrates a distal end of the actuation shafts extending from a wrist 980 located just proximal of the end effector. The wrist 980 can allow for fine movements and angulation of the end effector relative to the proximal end of the shaft 436. As shown in FIG. 7, the wrist 980 includes four articulation cables 982 that are spaced around a perimeter of the wrist 980. When actuated (e.g., pushed, pulled, rotated), the articulation cables 982 will cause articulation of the end effector (e.g., movement up, down, left, right, and combinations thereof) relative to the proximal end of the shaft 736. The articulation cables 982 are connected to articulation couplers 839, shown in FIG. 6, that are driven proximally and distally when the articulation gears G1, G2 are actuated by the first and second motors M1, M2. The wrist 980 also includes an upper rotary driver 984 that when actuated can cause the pair of jaws of the end effector to firmly close. The upper rotary driver 984 is coupled to the firm close gear G4a shown in FIGS. 5 and 6 such that rotation of the firm close gear G4a by the fourth motor M4 causes rotation of the rotary driver 984. The wrist 980 can also include a lower rotary driver 986 that when actuated can cause movement of a sled located at the end effector. The lower rotary driver 986 is coupled to the firing gear G5 shown in FIG. 6 and it likewise rotates in response to rotation of the firing gear G5. The illustrated wrist 980 further includes a linear pull cable 988 that is coupled to the quick close gear G4b shown in FIGS. 5 and 6 and that moves linearly in a proximal direction to cause rapid close of the pair of jaws of the end effector.

Figure 8:
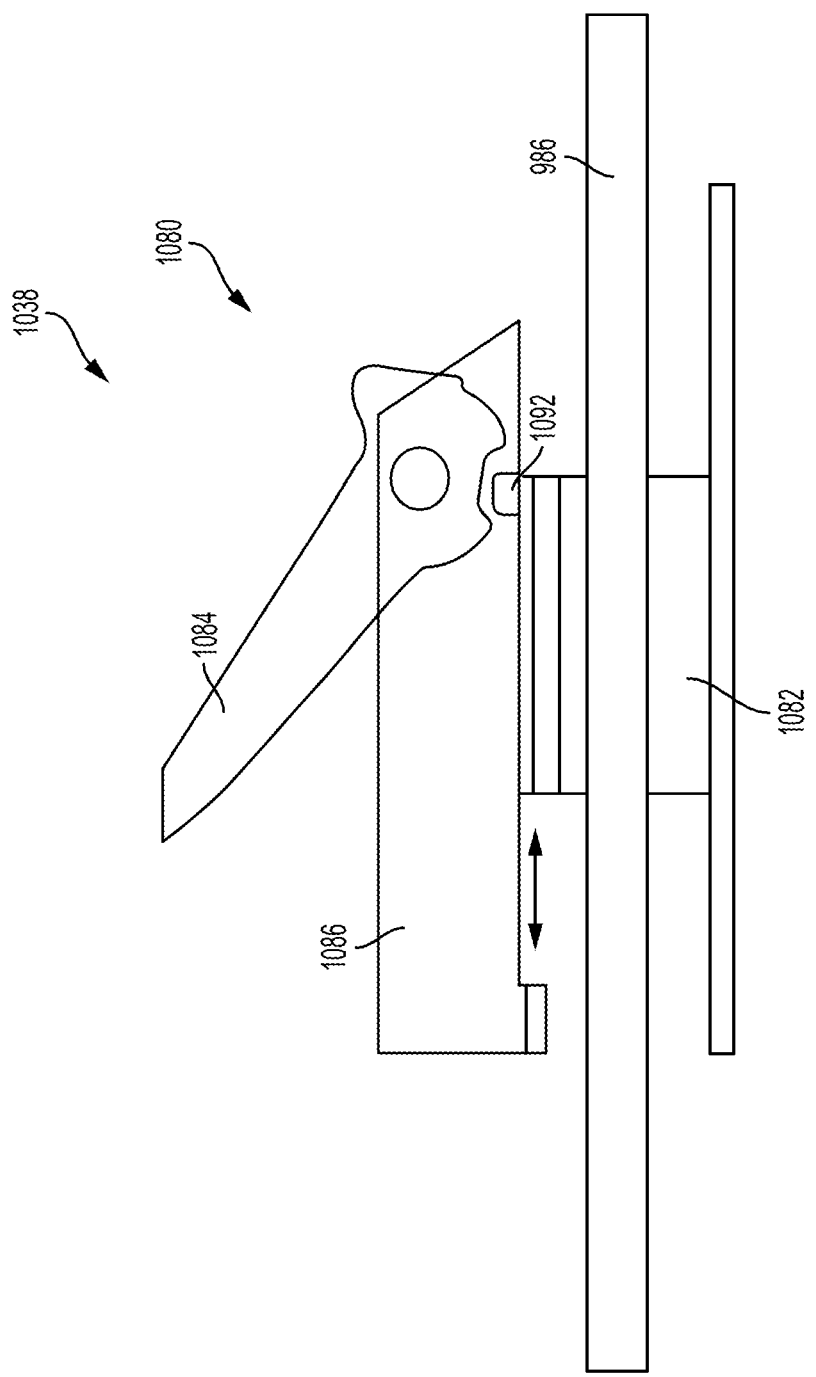
FIG. 8 is a partial side schematic view of one embodiment of an end effector having a knife actuation assembly.

FIG. 8 illustrates a portion of an end effector 1038 having a knife actuation assembly 1080 that includes a drive member 1082, a knife 1084, a knife sled 1086, and a lead screw or rotary driver 986. The drive member 1082 includes internal threads that are threadably coupled with the rotary driver 986. Such coupling can allow drive member 1082 to move along the rotary driver 986 when the rotary driver 986 is rotated. As discussed above, the rotary driver 986 can be actuated at the wrist 980, as shown in FIG. 7, thereby causing rotation of the rotary driver 986 and linear movement of the knife sled 1086 along the rotary driver 986. The rotary driver 986 is coupled to the firing gear G5 shown in FIGS. 5 and 6. The knife actuation assembly 1080 is configured to orient the knife 1084 in a cutting position when the drive member 1082 pushes the knife sled 1086 along the rotary driver 986 and to stow the knife 1084 when the drive member 1082 is moved proximally relative to the knife sled 1086. In operation, the rotary driver 986 is first rotated to advance the drive member 1082 distally along the rotary driver 986 thereby pushing the knife sled 1086 in the distal direction and angularly orienting the knife 1084 in the cutting position. At the end of the distal movement of the assembly 1080, the direction of rotation of the rotary driver 986 is reversed to retract the drive member 1082 proximally relative to the knife sled 1086, thereby causing the knife 1084 to rotate down into the stowed position, such as via interaction between an interface feature 1092 and the knife 1084.

Figure 9:
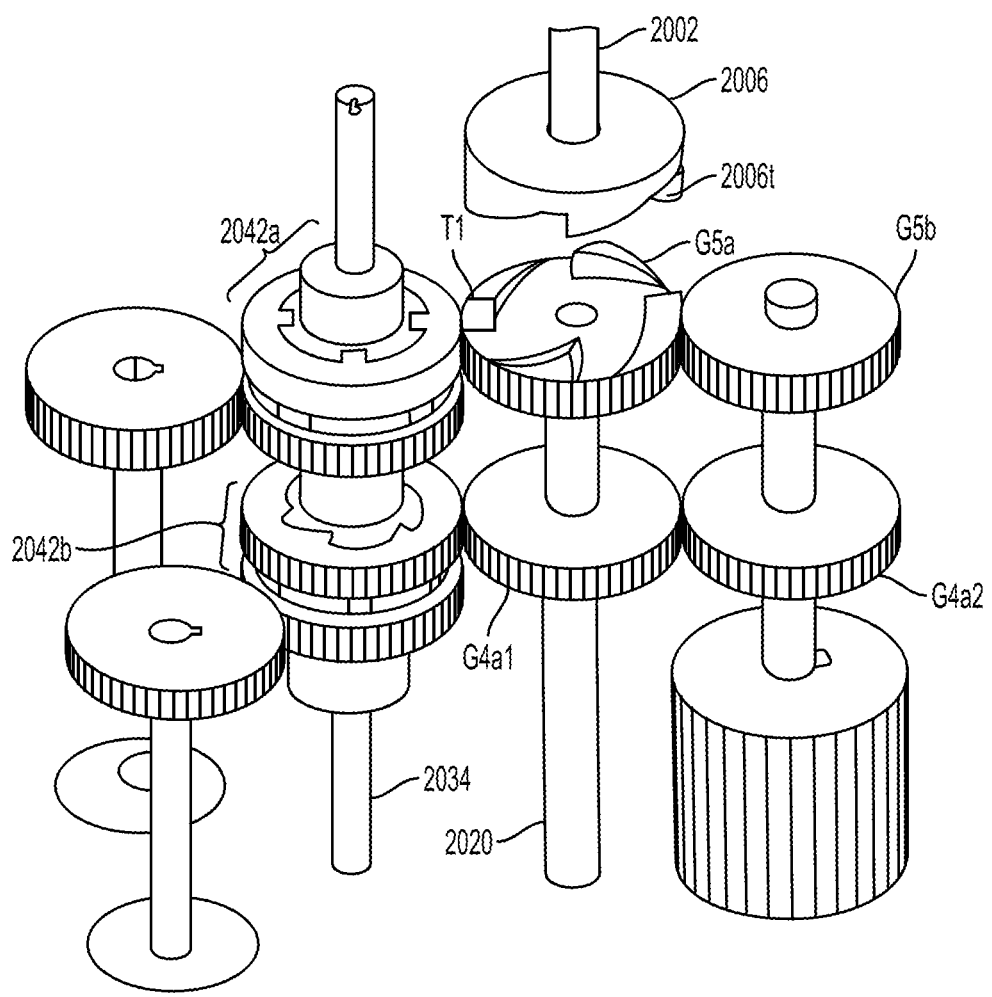
FIG. 9 is a perspective view of engaged gears of the puck of FIG. 5.

Two embodiments of bailout mechanisms are disposed in the puck 735 of FIG. 5 and are configured to engage, drive, reverse, and/or otherwise affect the actuation assembly 870 of FIG. 6. As illustrated in FIG. 5, a crank arm 2000 is disposed externally to an inner cover 735i of the puck 735 but inside of an outer cover 735c of the puck 735. The crank arm 2000 is disposed on a shaft 2002 extending through a hole in the inner cover 735i, and the crank arm 2000 is configured to pivot about the shaft 2002. The shaft 2002 is configured to be longitudinally slidable relative to the crank arm 2000, and has a button 2004 on a proximal end thereof. The button 2004 is configured to be manually pushed distally and is configured to couple onto the crank arm 2000 through various means, for example pins, tabs, hooks, etc., such that pivoting of the crank arm 2000 will rotate the button 2004 and thus the shaft 2002. The shaft 2002 has a one-way gear 2006 on a distal end thereof. The one-way gear 2006 has a circular shape with teeth 2006t extending distally from a distal surface thereon. The teeth 2006t are shaped such that they can engage corresponding teeth and apply a rotation force in one direction only, as illustrated in FIG. 9. The shaft 2002 is displaced longitudinally proximal to a drive shaft 2020, which has spur gears G5a and G4al fixed thereon. The spur gear G5a is rotatably coupled in a gear train with gears G5b and G5c, terminating in the firing gear G5. The spur gear G5a has teeth T1 extending proximally from a proximal surface thereon. The teeth T1 correspond in size and shape to the teeth 2006t and are configured to engage the teeth 2006t and receive a rotation force in one direction only. The spur gear G4a1 is rotatably coupled in a gear train with gears G4a2 and G4a3, terminating in the firm close gear G4a. The drive shaft 2020 is displaced longitudinally proximal to the third motor M3, and is rotatable free of the third motor M3.

A threaded shaft 2030 is disposed laterally from the drive shaft 2020 and is disposed longitudinally proximal to the motors M4, M5. A first end 2030a of the threaded shaft 2030 passes through a housing 2032 that is disposed on a shaft 2034 such that the threaded shaft 2030 is rotatable about its longitudinal axis relative to the housing 2032. The shaft 2034 has a series of gears fixed thereto and one or more additional gears and shafts engageably coupled to the series of gears and the shaft 2034 that engage the motors M4, M5. As motors M4, M5 are driven, the series of gears on the shaft 2034 are part of gear trains that engage and rotate the spur gear G5a and the spur gear G4a1 and ultimately the firing gear G5 and the firm close gear G4a. A second end 2030b of the threaded shaft 2030 passes through a displacement nut 2036, through a hole in the inner cover 735i, and through a bailout bolt 2038. The bailout bolt 2038 rests just outside of the inner cover 735i and is fixedly attached to the threaded shaft 2030 such that rotation of the bailout bolt 2038 rotates the threaded shaft 2030. The displacement nut 2036 is inside the housing 2032 and is rotatable on the threaded shaft 2030. First and second rods 2040a, 2040b (e.g., rigid rods such as metal rods) are pivotally fixed to the displacement nut 2036 on a proximal and distal side, respectively, in any of a variety of different ways, such as using pivot pins, embedding ends of the rods 2040a, 2040b therein, etc. The first and second rods 2040a, 2040b extend proximally and distally, respectively, from the displacement nut 2036 and fixedly terminate on first and second gear assemblies 2042a, 2042b (e.g., on first and second washers 2041a, 2041b thereof), respectively, that are both part of the gear series on the shaft 2034 and are longitudinally slidable on the shaft 2034. The first gear assembly 2042a couples through gear trains and shafts to the fifth motor M5 and is part of the gear train that rotates the firing gear G5. The second gear assembly 2042b couples through gear trains and shafts to the fourth motor M4 and is part of the gear train that rotates the firm close gear G4a. The first and second rods 2040a, 2040b can be pivotally fixed to the first and second gear assemblies 2042a, 2042b in any of a variety of ways, such as by pivot pins, embedding ends of the rods 2040a, 2040b therein, etc.

During normal operation as illustrated in FIG. 5, the gear assemblies 2042a, 2042b remain engaged in the gear trains connecting the motors M4, M5 to the firm close gear G4a and the firing gear G5, respectively. The motors M4, M5 can cause rotation of the firm close gear G4a and the firing gear G5 as explained above. The displacement nut 2036 rests at an inner edge of the inner cover 735i directly opposite the bailout bolt 2038 placed on the outside of the inner cover 735i. The threaded shaft 2030 does not rotate. The shaft 2002 remains in a proximal position, keeping the one-way gear 2006 disengaged from any surrounding gears and the button 2004 proximal to the crank arm 2000 and the inner cover 735i. The shaft 2002 is kept in a proximal position through friction interaction with the hole in the inner cover 735i through which the shaft 2002 passes, but the shaft 2002 can be kept proximal in any of a variety of ways, such as by a spring disposed around the shaft 2002 between the crank arm 2000 and the button 2004 that will bias the shaft 2002 and the button 2004 proximally, etc. The crank arm 2000 is immobile. The outer cover 735c covers all components that are external to the inner cover 735i.

When bailout is desired, such as when a malfunction occurs in the end effector in the firing and/or firm close functions, the outer cover 735c can be removed. A user can manually rotate the bailout bolt 2038, which will cause rotation of the threaded shaft 2030 because the bailout bolt 2038 is fixed on the threaded shaft 2030. As the threaded shaft 2030 rotates, the displacement nut 2036 will translate along the threaded shaft 2030 toward the housing 2032 because the displacement nut 2036 is rotatably placed on the threaded shaft 2030. Movement of the displacement nut 2036 will cause the metal rods 2040a, 2040b to pivot on the displacement nut 2036 and the gear assemblies 2042a, 2042b and force the gear assemblies 2042a, 2042b to move proximally and distally, respectively, on the shaft 2034 because the metal rods 2040a, 2040b will apply proximal and distal force to the gear assemblies 2042a, 2042b, respectively, as the metal rods 2040a, 2040b move toward the housing 2032 (and consequently toward the shaft 2034) with the displacement nut 2036. As the gear assemblies 2042a, 2042b move proximally and distally, respectively, the gear assemblies 2042a, 2042b will move out of engagement with the gear trains that engage the motors M4, M5 to the firm close gear G4a and the firing gear G5. As illustrated in FIG. 10, the gear assemblies 2042a, 2042b will move entirely out of engagement, thus severing any engagement between the motors M4, M5 and the gears G4a, G5. When the gear assemblies 2042a, 2042b have moved out of engagement of the gear trains, any actuation of the motors M4, M5 will have no effect on the actuation assembly 870. The button 2004 can then be manually pushed distally by a user, which will cause the shaft 2002 to move distally. The button 2004 will couple to the crank arm 2000, and the teeth 2006t on the one-way gear 2006 will engage the teeth T1 on the spur gear G5a. The crank arm 2000 can then be pivoted by a user to rotate the spur gear G5a, the shaft 2020, and the spur gear G4a1 together because they are all fixed to one another. The crank arm 2000 can be rotated, which causes rotation of the gear trains containing gears G5a, G5b, G5c, and G5 and gears G4a1, G4a2, G4a3, and G4a. The teeth 2006t, T1 only allow engagement and rotation in one direction, thus ensuring that rotation of the crank arm 2000 causes retraction and bailout of the firing and firm close functions.

In at least some embodiments, a hollow outer shaft 2044 extends around the shaft 2034 and rests distal to the gear assembly 2042b. The outer shaft 2044 is longitudinally slidable around the shaft 2034 and has one or more tabs 2044t on a distal end thereof that flare proximally. A channel 2046 sized to receive the shaft 2044 extends through a distal end of the puck 735. During normal operation, the outer shaft 2044 remains at rest, and the tabs 2044t remain inside the puck 735 and flare out to engage edges of the channel 2046 and prevent the outer shaft 2044 from sliding through the channel 2046. During bailout as the gear assembly 2042b is forced distally as described above, the gear assembly 2042b contacts a proximal end of the outer shaft 2044 and begins to force the outer shaft 2044 distally with continued movement of the gear assembly 2042b. As the outer shaft 2044 is forced distally, the tabs 2044t are forced into the channel 2046 and begin to compress because of their proximal flared shape, allowing the tabs 2044t and the outer shaft 2044 to enter the channel 2046. When the gear assembly 2042b is in its distal-most position, the tabs 2044t will pass entirely through the channel 2046, and the tabs 2044t and a distal end of the outer shaft 2044 will be positioned outside the puck 735, as illustrated in FIG. 10. Because of the proximal flared shape of the tabs 2044t, the tabs 2044t will engage an outer surface of the puck 735 and prevent the outer shaft 2044 from being moved entirely back into the puck 735. Protuberance of the outer shaft 2044 prevents the puck 735 from being correctly reengaged with the tool driver 440, which will prevent the puck 735 from being used again in a future operation after a bailout was required. Faulty pucks may be prevented from being used again through this mechanism.

Another bailout mechanism is illustrated in FIGS. 5 and 10 in the form of a tool receiver 2050. The tool receiver 2050 is configured to receive a tool, such as a hex wrench, and is displaced longitudinally proximal to the actuation assembly 870. The tool receiver 2050 is fixedly attached to a shaft 2050s that is rotatably engaged with the upper and lower rotary drivers 984, 986 through gear engagements inside of the actuation assembly 870. The tool receiver 2050 extends through the inner cover 735i. During normal operation, the tool receiver 2050 rotates with the actuation assembly 870 and is covered by the outer cover 735c. When bailout is desired, such as when a malfunction occurs in the end effector in the firing and/or firm close functions, the outer cover 735c can be removed, and a user can manually insert a tool such as a hex wrench into the tool receiver 2050 configured to receive such a tool. The user can then rotate the tool, which causes direct application of rotational force to the shaft 2050s and the upper and lower rotary drivers 984, 986. The user can reverse and/or retract the firing and firm close functions by continued rotation of the tool.

As mentioned above, the fourth motor M4 is configured to be shifted between operative engagement with the firm close gear G4a to effect firm closure of the end effector and the quick close gear G4b to effect quick closure of the end effector. As also mentioned above, the spur gear G4al is rotatably coupled in a gear train with gears G4a2 and G4a3, terminating in the firm close gear G4a. The spur gear G4al can be rotatably coupled in another gear train with gears G4a2 and G4a3, terminating in the quick close gear G4b. Shiftable gear G4a3 is configured to shift the fourth motor M4 by moving between these two gear trains for the quick close gear G4b and the firm close gear G4a. In other words, movement of the shiftable gear G4a3 between a first position, in which the shiftable gear G4a3 is in the gear train for the firm close gear G4a, and a second position, in which the shiftable gear G4a3 is in the gear train for the quick close gear G4b, causes the fourth motor M4 to shift between driving firm close of the end effector (when the shiftable gear G4a3 is in the first position) and quick close of the end effector (when the shiftable gear G4a3 is in the second position). Thus, only one of the two gear trains for quick close and firm close can be active at one time for the fourth motor M4 to drive. The shiftable gear G4a3 is slidably mounted on a shaft 2031 along which the shiftable gear G4a3 slides when moving between the first and second positions. FIGS. 5 and 10 illustrate the shiftable gear G4a3 in solid line in the first position and the shiftable gear G4a3 in phantom (dotted line) in the second position. FIG. 11 illustrates the shiftable gear G4a3 in phantom in the first position and the shiftable gear G4a3 in solid line in the second position. The first position of the shiftable gear G4a3 is the default position of the shiftable gear G4a3. In this way, regular, faster closure of the end effector is the default mode of closure.

In both of the first and second positions, the shiftable gear G4a3 is engaged with spool gear G4a2, as shown in FIGS. 5 and 11. In the first position, the shiftable gear G4a3 is engaged with a lower gear LG of the spool gear G4a2. In the second position, the shiftable gear G4a3 is engaged with an upper gear UG of the spool gear G4a2.

As shown in FIGS. 5 and 11, the puck 435 includes an electromagnet 2029 configured to be selectively actuated to shift the fourth motor M4 by moving the shiftable gear G4a3 between the first and second positions. The electromagnet 2029 as shown is in the form of a solenoid. The electromagnet 2029 is configured to be selectively actuated to generate a magnetic field within operative range of the shiftable gear G4a3. When the electromagnet 2029 is not generating the magnetic field, the shiftable gear G4a3 is in the first position. When the electromagnet 2029 is generating the magnetic field, the magnetic effect draws the shiftable gear G4a3 toward the electromagnet 2029 to move the shiftable gear G4a3 from the first position to the second position, e.g., to cause the shiftable gear G4a3 to slide up the shaft 2031. The shiftable gear G4a3 is thus made at least partially from a metal or other material configured to be affected by the magnetic field so as to allow the shiftable gear G4a3 to be drawn toward the electromagnet 2029. Removal of the electromagnetic field allows the shiftable gear G4a3 to move from the second position to the first position, e.g., to slide down the shaft 2031.

The electromagnet 2029 can be actuated in any of a variety of ways to generate the magnetic field. For example, the electromagnet 2029 can be configured to be operatively engaged with a current source in the tool driver (or elsewhere in the robotic surgical system of which the tool driver is a part) to which the puck 735 is releasably coupled, such as by a wire extending from the electromagnet 2029 to a coupling on the puck 735 that engages a corresponding coupling on the tool driver. The robotic surgical system's current source can be activated to actuate the electromagnet 2029. The robotic surgical system's current source can be activated in any number of ways, as will be appreciated by a person skilled in the art, such as by a user providing an input to an input tool of the robotic surgical system. For another example, the electromagnet 2029 can be configured to be electrically activated to alternately push and pull an actuation rod that is operatively coupled to the shiftable gear G4a3. When the electromagnet 2029 is inactive, the shiftable gear G4a3 is in the first position with the actuation rod located inside the electromagnet 2029. When the electromagnet 2029 is electrically activated, the actuation rod is pushed outward and advances the shiftable gear G4a3 to the second position.

One electromagnet 2029 is used in this illustrated embodiment to move the shiftable gear G4a3, but more than one electromagnet can be used to move the shiftable gear G4a3 or any of the other shiftable gears described herein. Using more than one electromagnet can allow a great force to be generated, which may facilitate movement of larger gears and/or help ensure gear movement.

FIG. 11 and FIG. 12 illustrate gear supports 2035 for the quick close gear G4b. The gear supports 2035 are configured to maintain vertical position of the quick close gear G4b along a shaft 2037 to which the quick close gear G4b is mounted while allowing rotation of the quick close gear G4b about the shaft 2037. The quick close gear G4b being maintained in a vertical position may facilitate engagement of the quick close gear G4b with the shiftable gear G4a3 since the quick close gear G4b will be located in a predictable vertical location for engagement with the shiftable gear G4a3 when the shiftable gear G4a3 moves to its second position. Two gear supports 2035 are shown, but another number of gear supports 2035 may be used. Additionally, any of the non-shiftable gears described herein that are rotatably mounted on a shaft can be coupled to at least one gear support configured to maintain vertical position of the gear to help ensure engagement of the gear with the one or more other gears engaged therewith.

As mentioned above, the third motor M3 is configured to be shifted between operative engagement with the shaft rotation gear G3a to effect causing rotation of the shaft 736 of the tool assembly and the head rotation gear G3b to effect rotation of the end effector relative to the shaft 736. As shown in FIG. 5, a gear G3 is rotatably coupled in a gear train with gears G3al and G3a2, terminating in the shaft rotation gear G3a. The gear G3 can be rotatably coupled in another gear train with gears G3al and G3a3, terminating in the head rotation gear G3b. Shiftable gear G3al is configured to shift the third motor M3 by moving between these two gear trains for the shaft rotation gear G3a and the head rotation gear G3b. In other words, movement of the shiftable gear G3al between a first position, in which the shiftable gear G3al is in the gear train for the shaft rotation gear G3a, and a second position, in which the shiftable gear G3al is in the gear train for the head rotation gear G3b, causes the third motor M3 to shift between driving rotation of the end effector (when the shiftable gear G3al is in the first position) and rotation of the shaft 736 and the end effector (when the shiftable gear G3al is in the second position). Thus, only one of the two gear trains for end effector rotation can be active at one time for the third motor M3 to drive. In both of the first and second positions, the shiftable gear G3al is engaged with gear G3, as shown in FIGS. 5 and 10. The shiftable gear G3al is slidably mounted on a shaft 2033 along which the shiftable gear G3al slides when moving between the first and second positions. FIGS. 5 and 10 illustrate the shiftable gear G3al in solid line in the first position, and FIG. 5 illustrates the shiftable gear G3al in phantom (dotted line) in the second position. The first position of the shiftable gear G3al is the default position of the shiftable gear G3al. In this way, rotation of the end effector relative to the shaft 736 is the default mode of end effector rotation.

As shown in FIGS. 5 and 10, the puck 735 includes an electromagnet 2035 configured to be selectively actuated to shift the third motor M3 by moving the shiftable gear G3al between the first and second positions. The electromagnet 2035 as shown is in the form of a solenoid and can be configured to be activated and deactivated to move the shiftable gear G3al similar to the electromagnet 2029 discussed above that can be activated and deactivated to move the shiftable gear G4a3. The shiftable gear G3al is thus made at least partially from a metal or other material configured to be affected by the magnetic field so as to allow the shiftable gear G3al to be drawn toward the electromagnet 2035.

Figure 13:
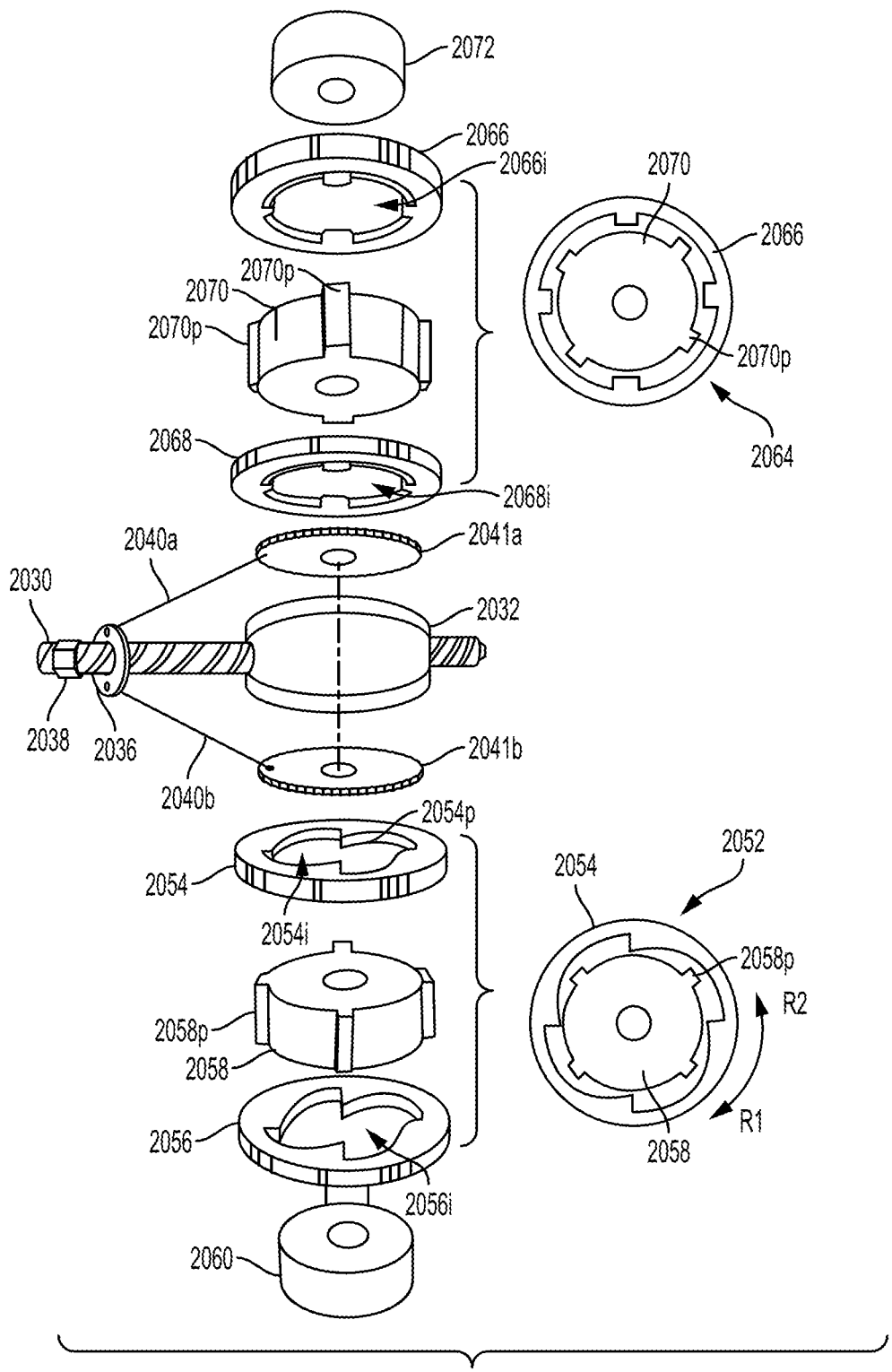
FIG. 13 is an exploded view of one embodiment of a closure assembly, a firing assembly, and a shifter of a puck.

As illustrated in FIG. 13, the puck 735 can include a closure assembly 2052 configured to limit an amount of torque provided to the tool assembly 430 by the fourth motor M4 for effecting closure of the end effector. The closure assembly 2052 is part of the second gear assembly 2042b (see FIGS. 5 and 10). The closure assembly 2052 is effective to limit the torque for both firm closure of the end effector and quick closure of the end effector.

The closure assembly 2052 includes a first gear 2054, a second gear 2056, and a coupler 2058 configured to limit an amount of torque provided to the tool assembly 430 by the fourth motor M4 when the second gear assembly 2042b is driven in a first direction (e.g., driven by the fourth motor M4 to rotate clockwise) and to limit an amount of torque provided to the tool assembly 430 by the fourth motor M4 when the second gear assembly 2042b is driven in a second, opposite direction (e.g., driven by the fourth motor M4 to rotate counterclockwise). The second gear assembly 2042b is driven by the fourth motor M4 for quick closure and for firm closure, so the closure assembly 2052 is configured to limit torque for both faster closure of the end effector effected using the quick close gear G4b and slower closure of the end effector effected using the firm close gear G4a. The coupler 2058 is disposed between the first and second gears 2054, 2056. A washer 2060 that is also part of the second gear assembly 2042b is disposed below the second gear 2056 to help with load distribution.

The coupler 2058 and the first and second gears 2054, 2056 can each be made from any a variety of materials. In an exemplary embodiment, the coupler 2058 can be plastic, and each of the first and second gears 2054, 2056 can be metal.

The first gear 2054 has an inner opening 2056i extending therethrough through which the shaft 2034 extends. The coupler 2058 has one or more protrusions 2058p extending radially outward from an outer perimeter thereof. The inner opening 2056i of the first gear 2054 is defined by a perimeter 2056p that has a shape configured to operatively engage the one or more protrusions 2058p to limit torque provided by the fourth motor M4 to the firm close and quick close gears G4a. G4b. The perimeter 2056p defines four lobes that correspond to the four protrusions 2058p of the coupler 2058. The coupler 2058 is non-rotatably attached to the shaft 2034. When the fourth motor M4 is actuated to drive rotation of a gear 2062 (see FIGS. 5 and 10) operatively coupled to the fourth motor M4 and thereby cause rotation of the gear train associated with the one of the firm close gear G4a and quick close gear G4b that is currently active (based on the position of the shiftable gear G4a3), the first and second gears 2054, 2056 rotate. The coupler 2058 does not rotate. The first and second gears 2054, 2056 are free to rotate in a counterclockwise direction (shown by arrow R2 in FIG. 13) without engaging the protrusions 2058p. Torque is thus not limited by the closure assembly 2052 when the fourth motor M4 drives counterclockwise rotation, which is associated with "backward" movement (e.g., end effector opening), thereby allowing for faster correction of, e.g., jaw closure on unintended tissue or on an improper amount of tissue. The perimeter 2054p defines a stop surface for each of the protrusions 2058p such that when the first and second gears 2054, 2056 rotate in a clockwise direction (shown by arrow R1 in FIG. 13), the protrusions 2058p will each abut their respective stop surfaces at a certain point during the gears' rotation. Torque provided by the fourth motor M4 will thus stop being provided to the one of the firm close gear G4a and quick close gear G4b that is currently active. The closure assembly 2052 is thus configured to limit torque. Clockwise rotation of the first and second gears 2054, 2056 is associated with "forward" movement (e.g., end effector closing), thereby allowing for closure to stop at a certain point so matter (e.g., tissue) clamped by the end effector is not overly compressed and/or so the end effector is not damaged by urging the jaws too much together.

The second gear 2056 is the same as the first gear 2054 and has a similar inner opening 2056i that has the shaft 2034 extending therethrough and that has a perimeter configured to operatively engage the protrusions 2058p of the coupler 2058.

As also illustrated in FIG. 13, the puck 735 can include a firing assembly 2064 configured to limit an amount of torque provided to the tool assembly 430 by the fifth motor M5 for effecting firing of the end effector. The firing assembly 2064 is part of the first gear assembly 2042a (see FIGS. 5 and 10). The firing assembly 2064 is effective to limit the torque for firing of the end effector. Although the puck 735 includes both the firing assembly 2064 and the closure assembly 2052, a puck can include only one of the firing assembly 2064 and the closure assembly 2052.

The firing assembly 2064 includes a first gear 2066, a second gear 2068, and a coupler 2070 configured to limit an amount of torque provided to the tool assembly 430 by the fifth motor M5 when the first gear assembly 2042a is driven in a first direction (e.g., driven by the fifth motor M5 to rotate clockwise) and to limit an amount of torque provided to the tool assembly 430 by the fifth motor M5 when the first gear assembly 2042a is driven in a second, opposite direction (e.g., driven by the fifth motor M5 to rotate counterclockwise). The coupler 2070 is disposed between the first and second gears 2066, 2068. A washer 2072 that is also part of the first gear assembly 2042a is disposed above the first gear 2066 to help with load distribution.

The coupler 2070 of the firing assembly 2064 is generally configured and used similar to the coupler 2058 of the closure assembly 2052, and the first and second gears 2066, 2068 of the firing assembly 2064 are generally configured and used similar to the first and second gears 2054, 2056 of the closure assembly 2052. Inner openings 2064i, 2066i of the first and second gears 2066, 2068 are configured to cooperate with the coupler 2070 to provide torque limits when the fifth motor M5 drives clockwise and counterclockwise rotation. Perimeters 2066p, 2068p of the first and second gears 2066, 2068 define stop surfaces for each of clockwise and counterclockwise rotation such that, unlike that discussed above regarding the closure assembly 2052, the firing assembly 2064 is configured to provide torque limits regardless of a direction that the fifth motor M5 drives gear rotation. The torque limits are the same in both the clockwise and counterclockwise directions, as defined by the shapes of the inner openings 2064i, 2066i and positions of the protrusions 2070p relative thereto.

As mentioned above, the puck 735 of FIG. 5 is configured to have the same torque limits for both firm closure and quick closure of the end effector. However, a puck of a tool assembly can be configured to independently limit the torque for firm closure of an end effector of the tool assembly and for quick closure of the end effector. This independent control of torque limits may allow for more precise control of firm closure and quick closure.

Figure 14:
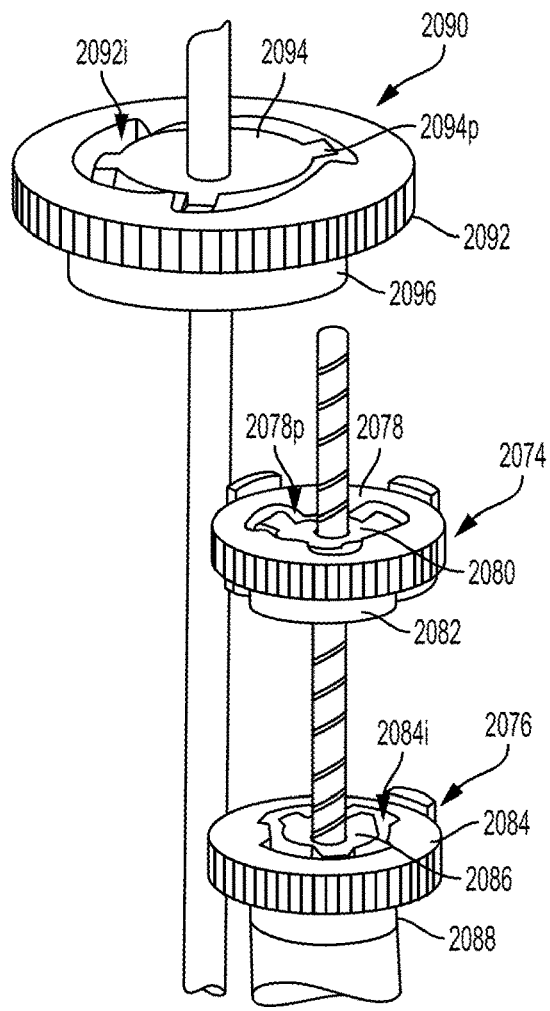
FIG. 14 is a perspective view of one embodiment of a closure assembly and a firing assembly.

FIG. 14 illustrates one embodiment of a closure assembly that independently limits the torque for firm closure of an end effector of a tool assembly and for quick closure of the end effector. The closure assembly includes a quick closure assembly 2074, shown in FIGS. 14 and 15, configured to limit the torque provided by a motor, e.g., the fourth motor M4 of FIG. 5, for quick closure of an end effector, e.g., the end effector 438 of FIG. 4. The quick closure assembly 2074 can be a final gear in a gear train for quick closure, e.g., the quick closure assembly 2074 can be used in place of the quick close gear G4b of FIG. 5. The closure assembly also includes a firm closure assembly 2076, shown in FIGS. 14 and 17, configured to limit the torque provided by a motor, e.g., the fourth motor M4 of FIG. 5, for quick closure of an end effector, e.g., the end effector 438 of FIG. 4. The firm closure assembly 2076 can be a final gear in a gear train for firm closure, e.g., the firm closure assembly 2076 can be used in place of the firm close gear G4a of FIG. 5.

Figure 15:
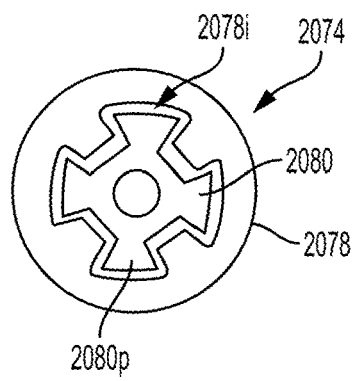
FIG. 15 is a top view of a quick closure assembly of the closure assembly of FIG. 14.
Figure 16:
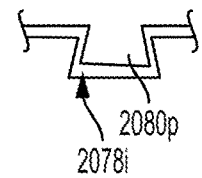
FIG. 16 is a portion of the quick closure assembly of FIG. 15.

As shown in FIGS. 14-16, the quick closure assembly 2074 includes a gear 2078 having an inner opening 2078i defined by a perimeter 2078p, a coupler 2080 having one or more protrusions 2080p extending radially outward from a perimeter thereof, and a washer 2082. The gear 2078 and the coupler 2080 are generally configured and used similar to that discussed above regarding the first gear 2066 and the coupler 2070 of FIG. 13. The inner opening 2078i is configured to cooperate with the coupler 2080 to provide a torque limit when the motor operatively coupled thereto drives clockwise and counterclockwise rotation. The perimeter 2078p defines stop surfaces for each of clockwise and counterclockwise rotation such that the quick closure assembly 2074 is configured to provide torque limits regardless of a direction that the motor drives gear rotation. The torque limits are the same in both the clockwise and counterclockwise directions, as defined by the shapes of the inner opening 2078i and positions of the protrusions 2080p relative thereto, that allows the gear 2078 to slip over the coupler 2080 when the protrusions 2080p abut the perimeter 2078p during gear 2078 rotation. The torque limits can instead be different in the clockwise and counterclockwise directions, as defined by the shapes of the inner opening 2078i and positions of the protrusions 2080p relative thereto, such as by having a first limit for "backward" movement and a second, lower limit for "forward" movement.

Figure 18:
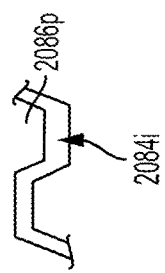
FIG. 18 is a portion of the firm closure assembly of FIG. 17.
Figure 17:
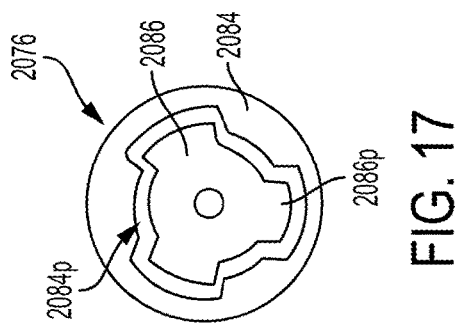
FIG. 17 is a top view of a firm closure assembly of the closure assembly of FIG. 14.

As shown in FIGS. 14, 17, and 18, the firm closure assembly 2076 includes a gear 2084 having an inner opening 2084i defined by a perimeter 2084p, a coupler 2086 having one or more protrusions 2086p extending radially outward from a perimeter thereof, and a washer 2088. The gear 2084 and the coupler 2086 are generally configured and used similar to that discussed above regarding the first gear 2066 and the coupler 2070 of FIG. 13. The inner opening 2084i is configured to cooperate with the coupler 2086 to provide a torque limit when the motor operatively coupled thereto drives clockwise and counterclockwise rotation. The perimeter 2084p defines stop surfaces for each of clockwise and counterclockwise rotation such that the firm closure assembly 2076 is configured to provide torque limits regardless of a direction that the motor drives gear rotation. The torque limits are the same in both the clockwise and counterclockwise directions, as defined by the shapes of the inner opening 2084i and positions of the protrusions 2086p relative thereto, that allows the gear 2084 to slip over the coupler 2086 when the protrusions 2086p abut the perimeter 2084p during gear 2084 rotation. The torque limits can instead be different in the clockwise and counterclockwise directions, as defined by the shapes of the inner opening 2084i and positions of the protrusions 2086p relative thereto, such as by having a first limit for "backward" movement (e.g., no limit at all) and a second, higher limit for "forward" movement.

As also illustrated in FIG. 14, the puck that includes the quick closure and firm closure assemblies 2074, 2076 can include a firing assembly 2090 configured to limit an amount of torque provided to the tool assembly by another motor (e.g., the fifth motor M5 of FIG. 5) for effecting firing of the end effector. The firing assembly 2090 is effective to limit the torque for firing of the end effector. The firing assembly 2090 can be a final gear in a gear train for firing, e.g., the firing assembly 2090 can be used in place of the firing gear G5 of FIG. 5. Although the puck includes all three of the firing assembly 2090 and the quick closure and firm closure assemblies 2074, 2076, a puck can include any one or two of the firing assembly 2090 and the quick closure and firm closure assemblies 2074, 2076.

Figure 20:
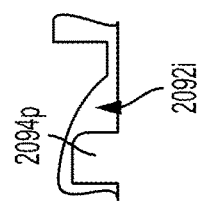
FIG. 20 is a portion of the firing assembly of FIG. 19.
Figure 19:
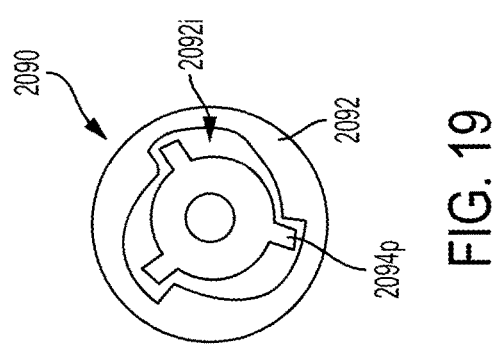
FIG. 19 is a flipped bottom view of the firing assembly of FIG. 14.

As shown in FIGS. 14, 19, and 20, the firing assembly 2090 includes a gear 2092 having an inner opening 2092i defined by a perimeter 2092p, a coupler 2094 having one or more protrusions 2094p extending radially outward from a perimeter thereof, and a washer 2096. The gear 2092 and the coupler 2094 are generally configured and used similar to that discussed above regarding the first gear 2054 and the coupler 2058 of FIG. 13. The inner opening 2092i is configured to cooperate with the coupler 2094 to provide a torque limit when the motor operatively coupled thereto drives clockwise and counterclockwise rotation. The perimeter 2092p defines a stop surface for only one of clockwise and counterclockwise rotation. The gear 2092 is free to rotate in a counterclockwise direction without engaging the protrusions 2094p. Torque is thus not limited by the firing assembly 2090 when the motor associated therewith drives counterclockwise rotation, which is associated with "backward" movement (e.g., knife retraction), thereby allowing for faster correction of, e.g., inadvertent cutting. The perimeter 2092p defines a stop surface for each of the protrusions 2094p such that when the gear 2092 rotates in a clockwise direction, the protrusions 2094p will each abut their respective stop surfaces at a certain point during the gear's rotation. Torque provided by the motor will thus stop driving the gear's rotation. The firing assembly 2090 is thus configured to limit torque. Clockwise rotation of the gear 2090 is associated with "forward" movement (e.g., knife advancement), thereby allowing for cutting to stop at a certain point so matter (e.g., tissue) firing does not occur too fast and/or the knife does not cut too fast.

Torque limiting mechanisms for closure (both for quick closure and firm closure) and for firing are discussed above. In alternative to all or in addition to any one or more of the closure and firing torque limiting mechanisms, a puck of a tool assembly can include one or more torque limiting mechanisms associated with one or more other functions of an end effector of the tool assembly. For example, the puck can include any one or more of a torque limiting mechanism for articulation, e.g., one torque limiting mechanism for both of the first and second articulation gears G1. G2 of FIG. 5 or a torque limiting mechanism for each of the first and second articulation gears G1, G2 of FIG. 5, and a torque limiting mechanism for rotation, e.g., one torque limiting mechanism for both of the shaft rotation gear G3a and the head rotation gear G3b of FIG. 5 or a torque limiting mechanism for each of the shaft rotation gear G3a and the head rotation gear G3b of FIG. 5.

A tool driver has a certain torque capacity, e.g., a predetermined maximum amount of available torque, that is appropriate for certain types of surgical tools configured to operably couple to the tool driver, e.g., a robust tool configured to receive an amount of torque up to the certain torque capacity such as an endocutter for stomach firings, but that is too high for other types of surgical tools configured to operably couple to the tool driver, e.g., less robust tools such as graspers, endocutters for vascular firings, and energy devices. A surgical tool configured to operably couple to the tool driver can be configured to communicate an identifier to the tool driver (e.g., transmit a signal thereto indicative of the identifier) that indicates a maximum amount of torque the tool can accept. The tool driver can be configured to not provide torque to the surgical tool over the maximum amount of torque that the tool can accept, thereby helping to ensure proper functioning of the tool without overloading the tool. To not provide too much torque to the tool driver in view of the tool's maximum amount of acceptable torque, the motors can be adjusted electrically or mechanically. The electrical adjustment of the motors can be accomplished, for example, by a series of small pager motors linked to each of the drive disk mechanisms associated with the motors configured to advance or retract a calming plate behind the mechanical torque limiting mechanism, thereby adjusting the motor's slip distance from the drive disk and thereby limiting its torque to the slip threshold. The mechanical adjustment of the motors can be accomplished, for example, by adjusting spacing in an axial direction of the torque limiters described above. By adjusting a gap between disks in these torque limiters, the threshold for slipping is affected, with a larger gap corresponding to a lower threshold.

Terminology

Figure 21:
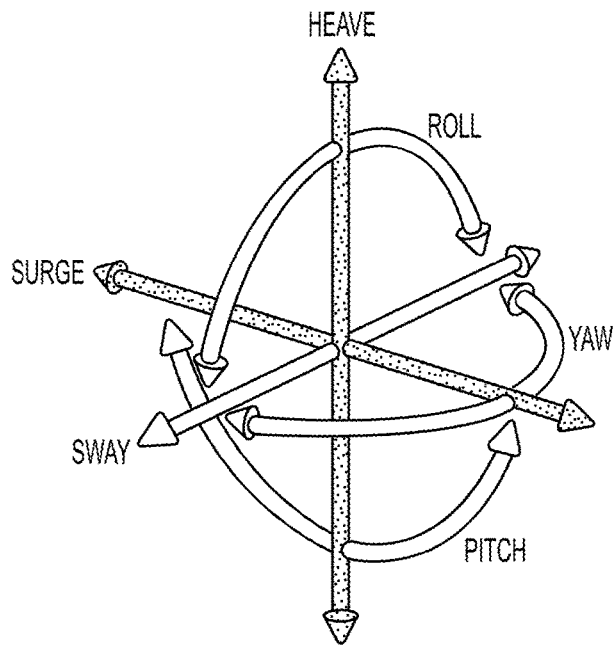
FIG. 21 is a graphical representation of terminology associated with six degrees of freedom.

There are a number of ways in which to describe the movement of a surgical system, as well as its position and orientation in space. One particularly convenient convention is to characterize a system in terms of its degrees of freedom. The degrees of freedom of a system are the number of independent variables that uniquely identify its pose or configuration. The set of Cartesian degrees of freedom is usually represented by the three translational or position variables, e.g., surge, heave, and sway, and by the three rotational or orientation variables, e.g., Euler angles or roll, pitch, and yaw, that describe the position and orientation of a component of a surgical system with respect to a given reference Cartesian frame. As used herein, and as illustrated in FIG. 21, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right. In a more general sense, each of the translation terms refers to movement along one of the three axes in a Cartesian frame, and each of the rotational terms refers to rotation about one of the three axes in a Cartesian frame.

Although the number of degrees of freedom is at most six, a condition in which all the translational and orientation variables are independently controlled, the number of joint degrees of freedom is generally the result of design choices that involve considerations of the complexity of the mechanism and the task specifications. For non-redundant kinematic chains, the number of independently controlled joints is equal to the degree of mobility for an end effector. For redundant kinematic chains, the end effector will have an equal number of degrees of freedom in Cartesian space that will correspond to a combination of translational and rotational motions. Accordingly, the number of degrees of freedom can be more than, equal to, or less than six.

With regard to characterizing the position of various components of the surgical system and the mechanical frame, the terms "forward" and "rearward" may be used. In general, the term "forward" refers to an end of the surgical system that is closest to the distal end of the input tool, and when in use in a surgical procedure, to the end disposed within a patient's body. The term "rearward" refers to an end of the surgical system farthest from the distal end of the input tool, and when in use, generally to the end farther from the patient.

The terminology used herein is not intended to limit the invention. For example, spatially relative terms, e.g., "superior," "inferior," "beneath," "below," "lower," "above,"

"upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes include various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown and described in various figures. An end effector is the part of a surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical systems described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as an input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical systems can also be used in open surgical procedures. As used herein, a surgical access point is a point at which the slave tool enters a body cavity through a tissue surface, whether through a cannula in a minimally invasive procedure or through an incision in an open procedure.

Computer Systems

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 22:
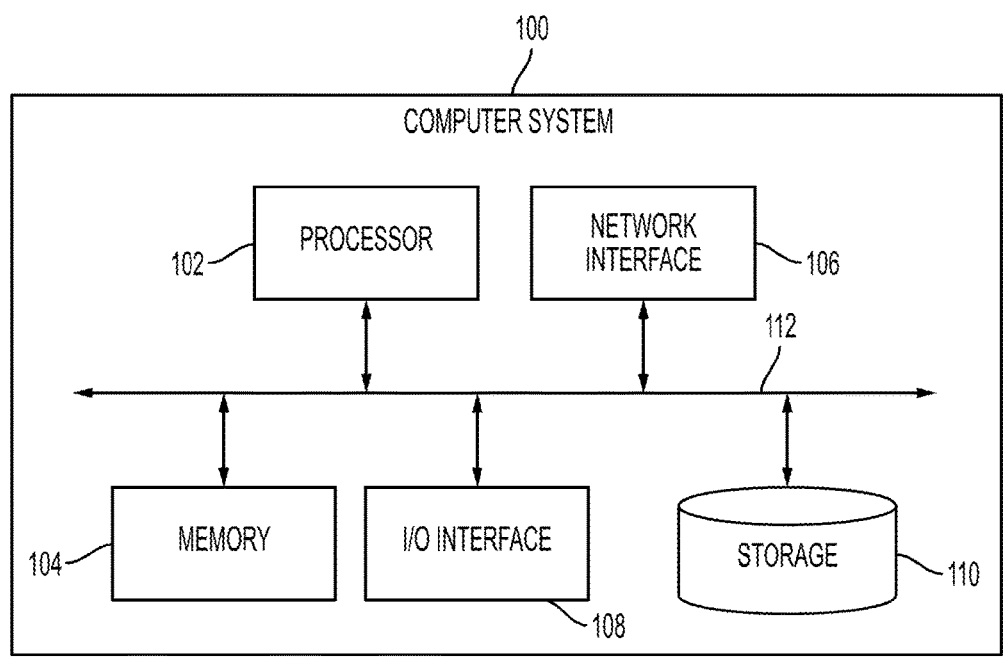
FIG. 22 is a schematic view of one embodiment of a computer system.

FIG. 22 illustrates one exemplary embodiment of a computer system 100. As shown, the computer system 100 includes one or more processors 102 which can control the operation of the computer system 100. "Processors" are also referred to herein as "controllers." The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (IO) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN) adapters. The IO interface(s) 108 can include one or more interface components to connect the computer system 100 with other electronic equipment. For non-limiting example, the IO interface(s) 108 can include high speed data ports, such as universal serial bus (USB) ports, 1394 ports, Wi-Fi, Bluetooth, etc. Additionally, the computer system 100 can be accessible to a human user, and thus the IO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value(s) are retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 22 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Reuse

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
   a first motor of a robotic surgical system, the robotic surgical system being configured to releasably and replaceably couple to a surgical tool, and the first motor having a maximum torque output;
   a first actuator of the robotic surgical system, the first motor being configured to apply an amount of torque to the first actuator and thereby cause movement of an end effector of the surgical tool, in which the amount of torque applied by the first motor to the first actuator does not exceed a first torque threshold that is less than the maximum torque output;
   a second actuator of the robotic surgical system, the first motor being configured to apply an amount of torque to the second actuator and thereby cause movement of the end effector of the surgical tool, in which the amount of torque applied by the first motor to the second actuator does not exceed a second torque threshold that is less than the maximum torque output and that is different from the first torque threshold;
   a second motor of the robotic surgical system; and
   a third actuator of the robotic surgical system;
   wherein the first motor is a single motor, and the second motor is configured to apply an amount of torque to the third actuator and thereby cause movement of the end effector of the surgical tool.

2. The system of claim 1, wherein the movement of the end effector caused by the amount of torque applied to the first actuator is different from the movement of the end effector caused by the amount of torque applied to the second actuator.

3. The system of claim 2, wherein the movement of the end effector caused by the amount of torque applied to the first actuator is closing of the end effector at a first speed, and the movement of the end effector caused by the amount of torque applied to the second actuator is closing the end effector at a second speed that is greater than the first speed.

4. The system of claim 1, further comprising a first torque limiting mechanism configured to prevent the amount of torque applied by the first motor to the first actuator from exceeding the first torque threshold; and
   a second torque limiting mechanism configured to prevent the amount of torque applied by the first motor to the second actuator from exceeding the second torque threshold.

5. The system of claim 4, wherein the first and second torque limiting mechanisms each include a rotatable gear.

6. The system of claim 1, wherein the first and second actuators each include a rotatable gear.

7. The system of claim 1, further comprising a tool driver including the first motor and the first and second actuators, the tool driver being configured to releasably and replaceably couple to a housing of the surgical tool.

8. The system of claim 1, wherein the surgical tool is a surgical stapler.

9. A surgical system, comprising:
   a motor of a robotic surgical system, the robotic surgical system being configured to releasably and replaceably couple to a surgical tool, and the motor having a maximum torque output;
   a first actuator of the robotic surgical system, the motor being configured to apply an amount of torque to the first actuator and thereby cause a first movement of an end effector of the surgical tool;
   a first torque limiting mechanism configured to prevent the amount of torque applied by the motor to the first actuator from exceeding a first torque threshold that is less than the maximum torque output;
   a second actuator of the robotic surgical system, the motor being configured to apply an amount of torque to the second actuator and thereby cause a second movement of the end effector of the surgical tool, the second movement being different from the first movement; and
   a second torque limiting mechanism configured to prevent the amount of torque applied by the motor to the second actuator from exceeding a second torque threshold that is less than the maximum torque output and that is different from the first torque threshold.

10. The system of claim 9, further comprising an additional motor of the robotic surgical system, and an additional actuator of the robotic surgical system;
    wherein the motor is a single motor, and the additional motor is configured to apply an amount of torque to the additional actuator and thereby cause movement of the end effector.

11. The system of claim 9, wherein the first torque limiting mechanism includes engaged first and second rotatable members; and
    the second torque limiting mechanism includes engaged third and fourth rotatable members.

12. The system of claim 9, wherein the first and second actuators each include a rotatable gear.

13. The system of claim 9, further comprising a tool driver including the motor and the first and second actuators, the tool driver being configured to releasably and replaceably couple to a housing of the surgical tool.

14. The system of claim 9, wherein the surgical tool is a surgical stapler.

15. A surgical method, comprising:
    rotating a first gear of a robotic surgical system to actuate a single motor of the robotic surgical system so as to output a first amount of torque and thereby cause an end effector of a surgical tool operatively coupled to the single motor to cause a first movement of the end effector in a body of a patient;
    preventing the first amount of torque output by the single motor from exceeding a first torque threshold that is less than the maximum torque output;
    rotating a second gear of the robotic surgical system to actuate the single motor so as to output a second amount of torque and thereby cause a second movement of the end effector in the body of the patient that is different from the first movement of the end effector; and
    preventing the second amount of torque output by the single motor from exceeding a second torque threshold that is less than the maximum torque output and that is different from the first torque threshold.

16. The method of claim 15, wherein preventing the first amount of torque output by the single motor from exceeding the first torque threshold includes engagement of first and second rotatable members; and
preventing the second amount of torque output by the single motor from exceeding the second torque threshold includes engagement of third and fourth rotatable members.

17. A surgical method, comprising:
actuating a single motor of a robotic surgical system to output a first amount of torque and thereby cause an end effector of a surgical tool operatively coupled to the single motor to cause a first movement of the end effector in a body of a patient;
preventing the first amount of torque output by the motor from exceeding a first torque threshold that is less than the maximum torque output;
actuating the single motor of the robotic surgical system to output a second amount of torque and thereby cause a second movement of the end effector in the body of the patient that is different from the first movement of the end effector;
preventing the second amount of torque output by the motor from exceeding a second torque threshold that is less than the maximum torque output and that is different from the first torque threshold; and
actuating an additional motor of the robotic surgical system to output a third amount of torque and thereby cause a third movement of the end effector in the body of the patient that is different from the first and second movements of the end effector.

18. The method of claim 15, further comprising releasably engaging a tool driver of the robotic surgical system to a proximal housing of the surgical tool, the end effector being located at a distal end of the surgical tool.

19. The method of claim 17, further comprising releasably engaging a tool driver of the robotic surgical system to a proximal housing of the surgical tool, the end effector being located at a distal end of the surgical tool.

* * * * *